US010751401B2

(12) United States Patent
Ganta et al.

(10) Patent No.: US 10,751,401 B2
(45) Date of Patent: Aug. 25, 2020

(54) **ATTENUATED VACCINES TO PROTECT AGAINST TICK-BORNE *EHRLICHIA* SPECIES INFECTIONS**

(71) Applicant: Kansas State University Research Foundation, Manhattan, KS (US)

(72) Inventors: Roman R. Ganta, Manhattan, KS (US); Chuanmin Cheng, Manhattan, KS (US); Arathy D. S. Nair, Manhattan, KS (US); Deborah Jaworski, Stillwater, OK (US); Suhasini Ganta, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 16/556,902

(22) Filed: Aug. 30, 2019

(65) Prior Publication Data

US 2020/0000906 A1 Jan. 2, 2020

Related U.S. Application Data

(62) Division of application No. 16/106,546, filed on Aug. 21, 2018, now Pat. No. 10,434,161, which is a division of application No. 15/544,090, filed as application No. PCT/US2016/013933 on Jan. 19, 2016, now abandoned.

(60) Provisional application No. 62/104,998, filed on Jan. 19, 2015.

(51) Int. Cl.
*A61K 39/00* (2006.01)
*A61K 39/02* (2006.01)

(52) U.S. Cl.
CPC .... *A61K 39/0233* (2013.01); *A61K 2039/522* (2013.01); *A61K 2039/552* (2013.01); *A61K 2039/575* (2013.01)

(58) Field of Classification Search
CPC ........ A61K 2039/522; A61K 2039/552; A61K 2039/575; A61K 39/0233
See application file for complete search history.

(56) References Cited

U.S. PATENT DOCUMENTS

2005/0158277 A1 7/2005 Cinquegrani et al.
2013/0122041 A1 5/2013 Harrus et al.

OTHER PUBLICATIONS

The International Search Report and Written Opinion dated Jun. 10, 2016, in PCT/US2016/013933, filed Jan. 19, 2016.
Cheng, Chuanmin "Targeted and Random Mutagenesis of Ehrlichia Chaffeensis for the Identification of Genes Required for in vivo Infection," Plos Pathogens, Feb. 14, 2013, vol. 9 (2).
UniProtKB entry Q2GGG5_EHRCR, Uncharacterozed phage protein, putative, Ehrlichia chaffeensis str. Sapulpa, Mar. 21, 2006.
Genbank Accession No. KJ567138, "Mutant Anaplasma marginale transposon Himar1, complete sequence," Apr. 15, 2014.
Office Action in corresponding U.S. Appl. No. 15/544,090, dated May 15, 2018.
Office Action in corresponding U.S. Appl. No. 16/106,546, dated Sep. 19, 2018.
Office Action in corresponding U.S. Appl. No. 16/106,546, dated Nov. 27, 2018.
McGill et al. PLoS One 11 (2), e1048229, pp. 1-15, 2016.

*Primary Examiner* — Sarvamangala Devi
(74) *Attorney, Agent, or Firm* — Hovey Williams LLP

(57) ABSTRACT

Attenuated vaccines to protect vertebrate animals and people against tick-born rickettsial, *Ehrlichia* and *Anaplasma* species infections is disclosed. Also disclosed are methods to modify the organism to achieve the desired immunity through the modification of a novel genetic region involved in pathogenesis. These compounds represent a needed vaccine against an organism causing life-threatening febrile illness in humans and animals, and also represent the potential to develop new classes of drugs targeting the gene products of genes Ech_0379 and Ech_0230, and their homologs of other related rickettsial pathogens.

14 Claims, 22 Drawing Sheets

Specification includes a Sequence Listing.

Day 7 Post-Challenge

Ech 0660 Vaccinated | Non-Vaccinated

|  | Group 1 | Group 2 | Group 3 |
|---|---|---|---|
| Mock | 1.31% | 1.38% | 0.853% |
| *E. chaff* | 8.47% | 5.59% | 2.03% |

CD4 →

Group 3

WT *E. chaff* or
Ech_0480
Challenge: Tick

● WT_1
◄ WT_2
► Ech_0480_1
♦ Ech_0480_2

Total IgG (ng/mL)

10000
8000
6000
4000
2000
0

0 3 7 14 21 28 35

Days Post Vaccination/Challenge

ATTENUATED VACCINES TO PROTECT AGAINST TICK-BORNE *EHRLICHIA* SPECIES INFECTIONS

CROSS-REFERENCE TO RELATED APPLICATIONS

The present application is a divisional of U.S. Ser. No. 16/106,546, filed Aug. 21, 2018 and issued on Oct. 8, 2019 as U.S. Pat. No. 10,434,161, which is a divisional of U.S. Ser. No. 15/544,090, now abandoned, which is the U.S. National Stage of International Patent Application No. PCT/US2016/013933, filed Jan. 19, 2016, which claims the priority benefit of U.S. Provisional Patent Application Ser. No. 62/104,998, filed Jan. 19, 2015, entitled ATTENUATED VACCINES TO PROTECT AGAINST TICK-BORNE *EHRLICHIA* SPECIES INFECTIONS, each of which is incorporated by reference in its entirety herein.

FEDERALLY SPONSORED RESEARCH OR DEVELOPMENT

This invention was made with government support under grant # AI070908 awarded by the National Institute of Health. The United States government has certain rights in the invention.

SEQUENCE LISTING

The following application contains a sequence listing in computer readable format (CRF), submitted as a text file in ASCII format entitled "47025-PCTSequenceListing," created on Jan. 19, 2016, as 1,526 KB. The content of the CRF is hereby incorporated by reference.

BACKGROUND OF THE INVENTION

Field of the Invention

The present invention relates to vaccines against *Ehrlichia* and *Anaplasma* species infections in vertebrate animals and people and the development of a new class of drugs.

Description of Related Art

*Ehrlichia chaffeensis* is an obligate intracellular gram-negative species of rickettsial bacteria. *E. chaffeensis* is an *Amblyomma americanum* tick-transmitted rickettsial pathogen causing persistent infections in people and several other vertebrate animals. The disease caused by *E. chaffeensis* in people is referred as the human monocytic ehrlichiosis (HME). People with HME may exhibit flu like symptoms. HME in people can cause a life-threatening febrile illness and is associated with significant morbidity, especially in people with compromised immunity. About 40-60% of cases of HME require hospitalization, and fatality rates are estimated to be around 3%. White-tailed deer is the reservoir host for the pathogen, while humans, dogs and other vertebrate hosts, such as coyotes and goats, are regarded as the incidental hosts, similar to humans.

*E. chaffeensis* infections are a major concern for people with compromised immunity, as they develop a more severe disease which also results in a higher case-fatality rate. Further, because *E. chaffeensis* infects monocytes and macrophages and the pathogen is viable in refrigerated blood, people undergoing blood transfusions and organ transplantations are also at high risk in acquiring the pathogen and can develop a severe life threatening HME disease. The limited therapeutic option of only a single class of antibiotics and the non-availability of vaccines to prevent the infection are the added challenges for both humans and companion animals. The vaccine development is complicated due to limited understanding of the influence of the host on the pathogen phenotype and immunogenicity, and the limited knowledge about the pathogen antigens involved in stimulating protective immunity. Deer, dog and *A. americanum* tick infection studies are ideal for mapping genes essential to *E. chaffeensis* growth and persistence in vertebrate and tick hosts as they are recognized as the reservoir, an incidental host and the tick vector, respectively. In particular, the dog is an ideal incidental host model similar to humans in acquiring infections with *E. chaffeensis* from an infected *A. americanum* tick. *E. chaffeensis* infections in deer and dog are very similar in exhibiting clinical symptoms, rickettsemia levels and in their antibody responses.

To date, there are no reports in the literature which describe the vaccine development against *E. chaffeensis* infections in humans and dogs. Currently, treatment with the only available antibiotic class and the supporting care are the only options of controlling the disease in people or dogs.

SUMMARY OF THE INVENTION

The present invention relates to the development of a new class of drugs derived from targeting gene regions in *Ehrlichia* species. The invention broadly includes the methodology for generating attenuated mutant strains of organisms. The utility of these attenuated organisms comes from their application as a new class of vaccines to protect people and other vertebrate animals against infection. Herein, we disclose the methodology involved in developing these mutant organisms, how these modifications result in attenuated strains, a description of the pathogen-specific antibody and $CD4^+$ T cell responses they elicit, and the resultant protective immunity against secondary challenges.

Described herein are immunogenic compositions useful to elicit an immune response against *Ehrlichia* infection (e.g., tick-transmitted *E. chaffeensis* infection or other rickettsial infections) in a subject. The compositions generally comprise live, attenuated *E. chaffeensis* dispersed in a pharmaceutically-acceptable carrier. The live, attenuated *E. chaffeensis* comprises a mutation in one or more target genes that results in attenuated growth of the bacterium in a vertebrate host organism.

Methods of inducing an immune response against *Ehrlichia* infection in a subject are also described herein. The methods generally comprise administering an immunogenic composition according to any one of embodiments described herein to the subject, for protection and/or treatment against tick-transmitted *E. chaffeensis* infection or other rickettsial infections.

Also described herein are kits for inducing an immune response against *Ehrlichia* infection in a subject. The kits generally comprise an immunogenic composition according to any one of embodiments described herein, instructions for administering the immunogenic composition to the subject.

Use of an immunogenic composition according to any one of embodiments described herein for inducing an immune response against *Ehrlichia* infection in a subject is also described herein.

BRIEF DESCRIPTION OF THE DRAWING FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
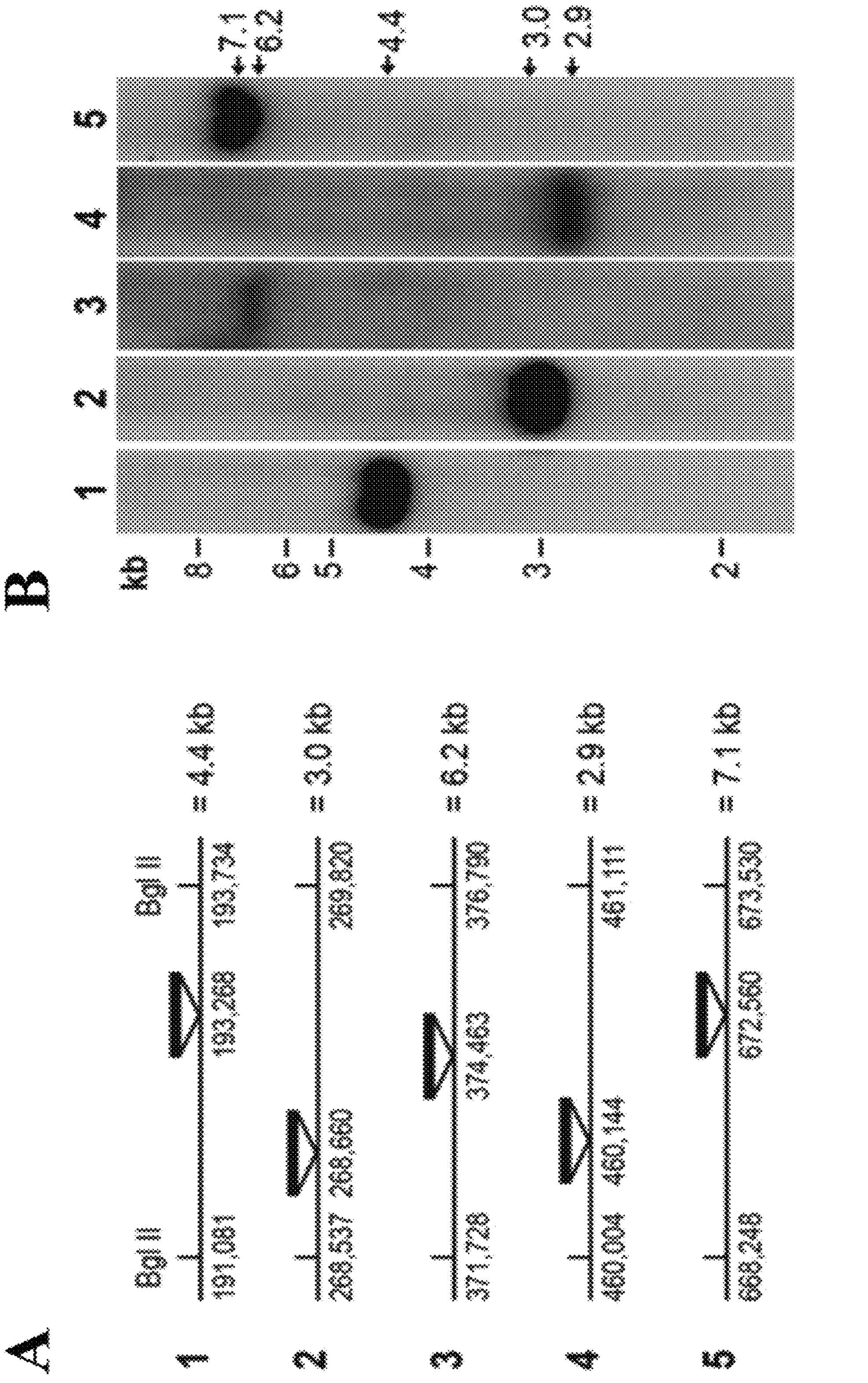
FIG. 1 is (A) an illustration of the insertions and (B) verification of clonal purity amongst five mutant strains by Southern blot.
Figure 2A:
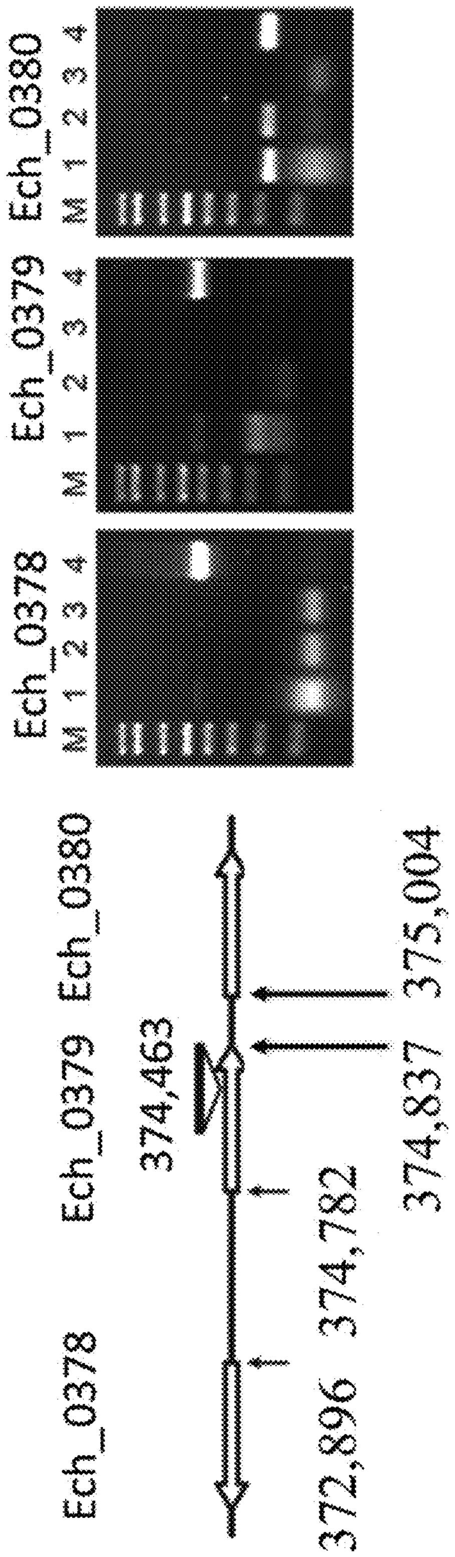
FIG. 2A is an illustration for the insertion and transcriptional analysis of genes neighboring transposon insertion sites by semi-quantitative RT-PCR.
Figure 2B:
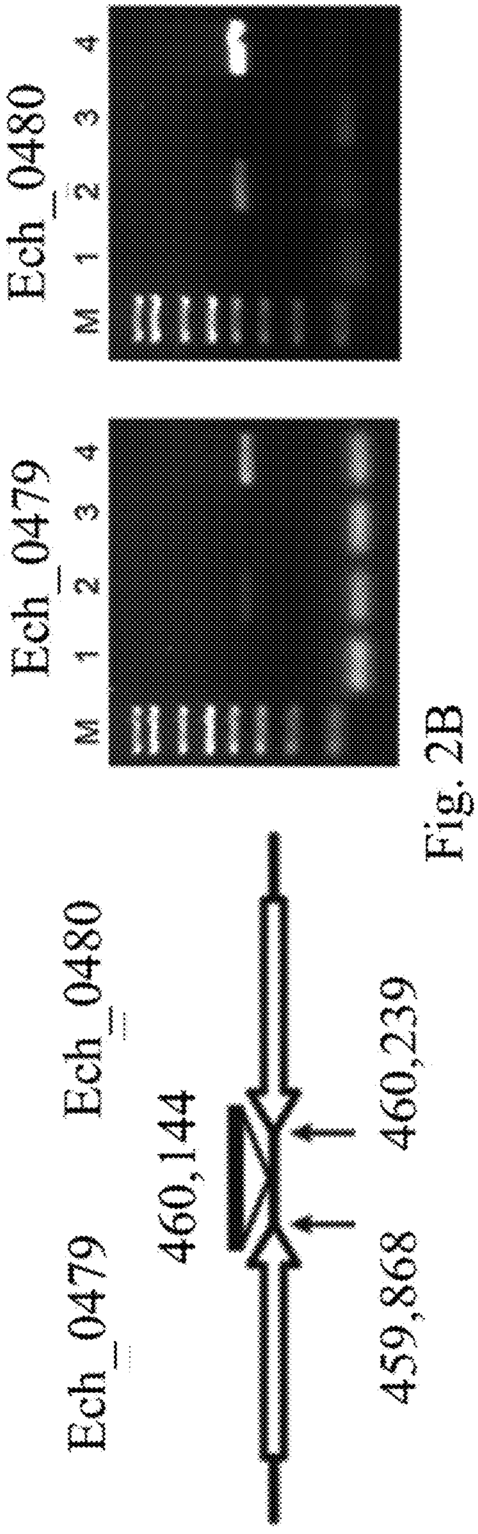
FIG. 2B is an illustration for the insertion and transcriptional analysis of genes neighboring transposon insertion sites by semi-quantitative RT-PCR.
Figure 2C:
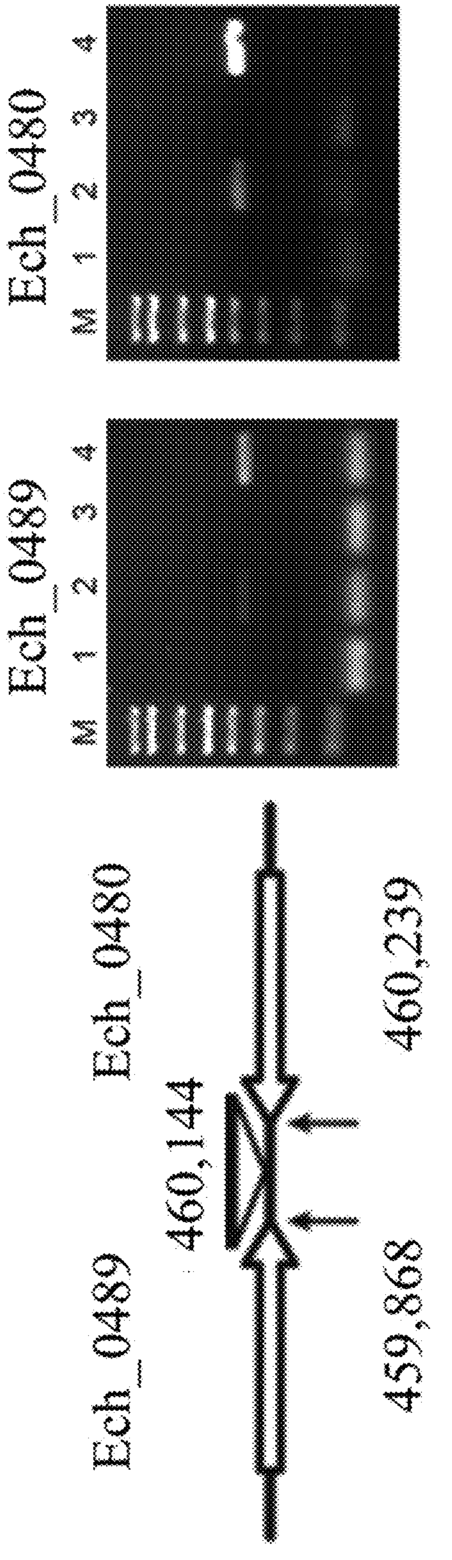
FIG. 2C is an illustration for the insertion and transcriptional analysis of genes neighboring transposon insertion sites by semi-quantitative RT-PCR.
Figure 2D:
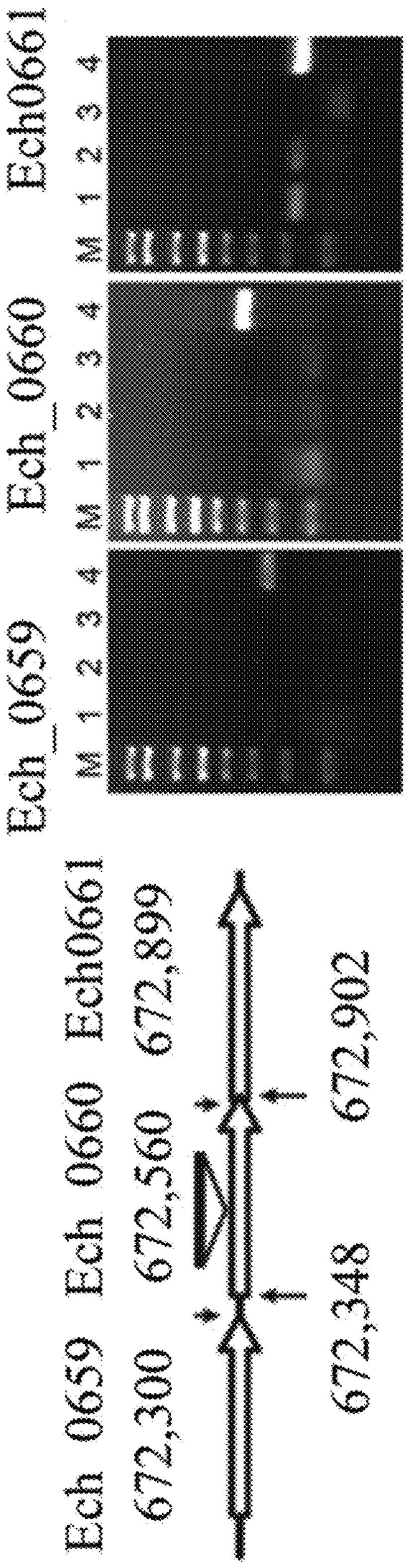
FIG. 2D is an illustration for the insertion and transcriptional analysis of genes neighboring transposon insertion sites by semi-quantitative RT-PCR.
Figure 2E:
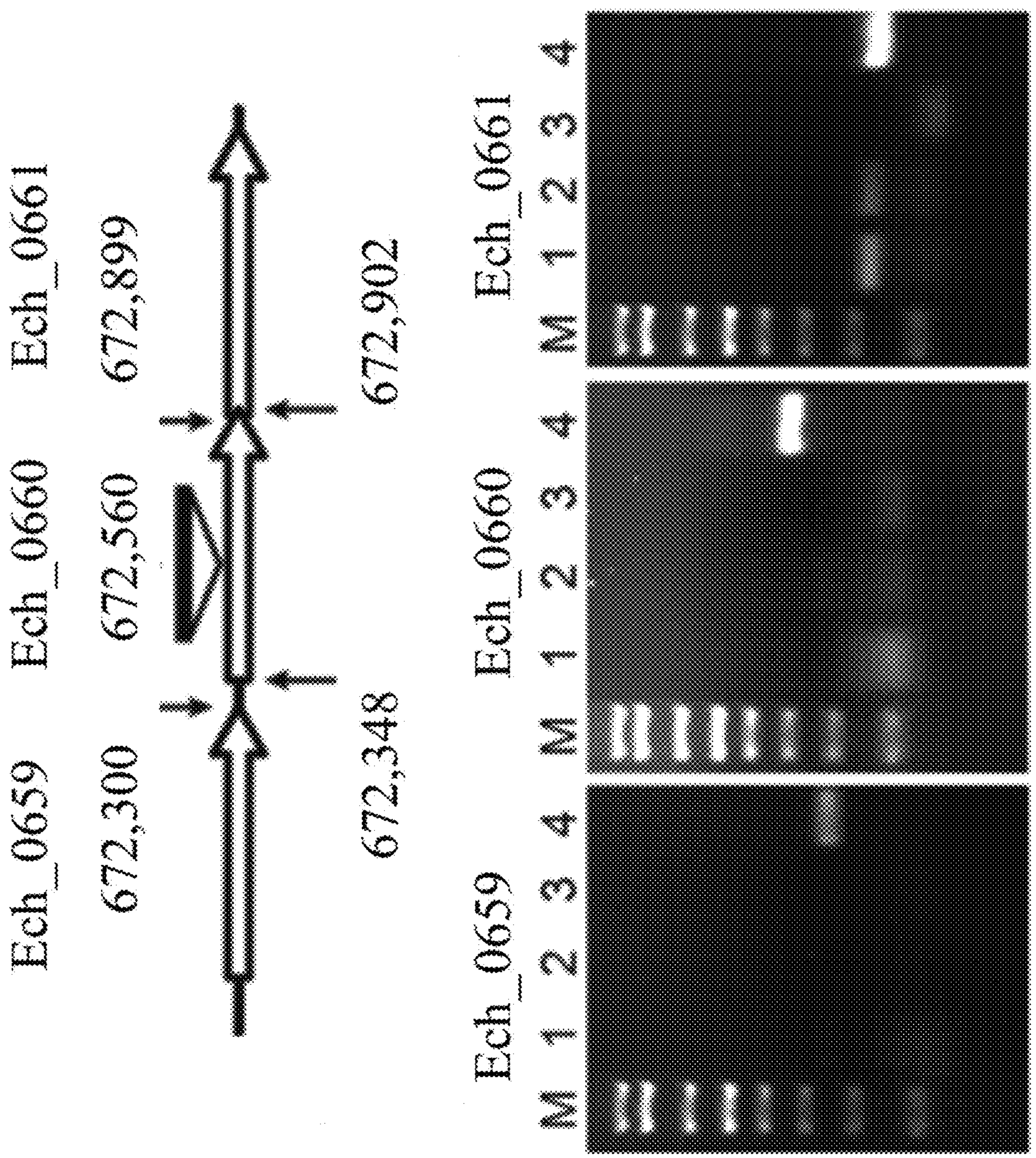
FIG. 2E is an illustration for the insertion and transcriptional analysis of genes neighboring transposon insertion sites by semi-quantitative RT-PCR.

In more detail, the invention is concerned with attenuated *Ehrlichia* strains. In one or more embodiments, the invention is concerned with attenuated *E. chaffeensis*. In particular, the invention is concerned with live attenuated mutant *E. chaffeensis* strains, and corresponding immunogenic compositions for eliciting immune responses against *Ehrlichia* infection, and particularly tick-transmitted *E. chaffeensis* infection. In one or more embodiments, the live attenuated mutants are *E. chaffeensis* str. Arkansas (Genbank CP000236.1, incorporated by reference herein, SEQ ID NO:1). In one or more embodiments, the attenuated mutant strain of *E. chaffeensis* comprises a mutation in one or more genes that results in attenuated growth of the bacterium in a vertebrate host organism. In one or more embodiments, the mutation is an insertion in gene protein coding region of a target gene itself or in sequences responsible for, or involved in, controlling gene expression. In another aspect, the mutation results in an insertion in the gene, wherein the insertion causes altered expression of a gene product encoded by the genes near the insertion causing an inactive gene product encoded by the mutated gene. In one or more embodiments, the attenuated mutant strain of *E. chaffeensis* comprises an insertion mutation in one or more genes that results in attenuated growth of the bacterium in the host organism. In one or more embodiments, the mutation is stably incorporated into the mutant strain's genome. In one or more embodiments, the insertion mutation is transposon-based, random mutagenesis generating a stable insertion mutation in one or more *E. chaffeensis* genes. In one or more embodiments, the mutation causes transcriptional inactivation of a bacterial membrane protein gene in the mutated strain.

In one or more embodiments, the gene is selected from the group consisting of Ech_0660 (SEQ ID NO:2), Ech_0379 (SEQ ID NO:4), and Ech_0230 (SEQ ID NO:6). In one or more embodiments, the attenuated mutant strain of *E. chaffeensis* comprises a mutation in the phage-like structure connector protein encoding gene, Ech_0660 (SEQ ID NO:2). In one or more embodiments, the attenuated mutant strain of *E. chaffeensis* comprises an insertion mutation in the phage-like protein encoding gene, Ech_0660 (SEQ ID NO:2), and more preferably a transposon (random) insertion mutation in Ech_0660 (SEQ ID NO:2). In one or more embodiments, the attenuated mutant strain of *E. chaffeensis* comprises an insertion mutation in the putative Na+/H+ antiporter protein encoding gene, Ech_379 (SEQ ID NO:4), and more preferably a transposon (random) insertion mutation in Ech_0379 (SEQ ID NO:4). In one or more embodiments, the attenuated mutant strain of *E. chaffeensis* comprises an insertion mutation in the putative membrane protein encoding gene, Ech_0230 (SEQ ID NO:6), and more preferably a transposon (random) insertion mutation in Ech_0230 (SEQ ID NO:6). In one or more embodiments, the mutation results in inhibition and/or inactivation of transcription and/or translation of a gene product (protein) selected from the group consisting of SEQ ID NO:3 (Genbank ABD45123.1), SEQ ID NO:5 (Genbank ABD44646), and SEQ ID NO:7 (Genbank ABD45256.1).

In one or more embodiments, the insertion sequence comprises at least one heterologous sequence, and preferably at least one reporter stably incorporated therein. In one or more embodiments, the heterologous sequence comprises an in vivo inducible promoter, and preferably a promoter related to a heterologous transcription regulator gene, such as from a different *Ehrlichia* strain or species or *Anaplasma* species. In one or more embodiments, the heterologous sequence is a promoter from *Anaplasma marginale* transcription regulator gene. In one or more embodiments, the heterologous sequence is fused to at least one reporter gene, such as a fluorescence gene, antibiotics resistance gene, and the like. Reporter genes assist in identification of successfully generated mutant strains from the wild type (wt) by making the mutant bacteria resistant to an antibiotic (e.g., Streptomycin/Spectinomycin resistance gene) or give off a fluorescence signal (e.g., mCherry fluorescence gene, GFUuv fluorescence gene). In one or more embodiments, the insertion sequence is engineered by molecular cloning of these fragments into a plasmid vector, followed by replication to obtain a large quantity of the engineered plasmid. This plasmid can then be used to generate the mutant strain. In one or more embodiments, the mutation comprises insertion of SEQ ID NO:8 into the target gene. In one or more embodiments, the mutation comprises insertion of SEQ ID NO:9 into the target gene.

In one or more embodiments, the attenuated mutant strain of *E. chaffeensis* is generated by transpositional insertion causing altered expression of several genes positioned upstream and downstream to the insertion sites. In one or more embodiments, the attenuated mutant strain of *E. chaffeensis* comprises one or more mutated genes selected from the group consisting of SEQ ID NO:10 (mutated sequence for Ech_0660), SEQ ID NO:11 (mutated sequence for Ech_0379), and SEQ ID NO:12 (mutated sequence for Ech_0230; note that the insertion mutant in Ech_0230 is inserted 17 nt downstream from the wild type stop codon). The effect of the inactivation of these genes causes attenuation of the organism's growth in vertebrate hosts, but does not impact its acquisition and persistence in ticks. In one or more embodiments, the invention is concerned with other live attenuated mutant strains of *Ehrlichia canis, Ehrlichia ewingii, Ehrlichia muris, Ehrlichia muris*-like agent infectious to humans, *Anaplasma phagocytophilum, Anaplasma marginale*, and/or *Anaplasma platys*. The mutants comprise a mutation in a gene homologous to *E. chaffeensis* gene Ech_0660, Ech_0379, or Ech_230, which results in attenuated growth of the bacterium in a vertebrate host organism.

Regardless, the resulting mutant *E. chaffeensis* can be used in immunogenic compositions to elicit an immune response against *Ehrlichia* infection in a subject. In some embodiments, the mutant *E. chaffeensis* can be used as a vaccine for immunizing a subject against *Ehrlichia* infection. The term "vaccine" is used interchangeably herein with "immunogenic composition" and refers to compositions capable of eliciting partial or complete immunogenic protection against a disease or condition in the subject to which it has been administered. Although vaccines are generally considered prophylactic, the vaccines may be used for therapeutic treatment of a disease or a condition. The terms "prophylactic" or "prevent," as used herein, refer to vaccines that are intended to inhibit or ameliorate the effects of a future infection or disease to which a subject may be exposed (but is not currently identified as having been infected with). In other words, for prophylactic use, the subject generally does not (yet) show observable signs/symptoms of infection prior to administration of the immunogenic composition. In some cases the vaccine may prevent the development of observable morbidity from infection (i.e., near 100% prevention). In other cases, the vaccine may only partially prevent and/or lessen the extent of morbidity due to the infection (i.e., reduce or mitigate the severity of the symptoms and/or effects of the infection, and/or reduce or mitigate the duration of the infection/symptoms/effects). In either case, the vaccine is still considered to "prevent" the target infection or disease in the context of this disclosure. Conversely, the terms "therapeutic" or "treat," as used herein, refer to vaccines that are intended to produce a beneficial change in an existing condition (e.g., infection, disease) of a subject, such as by reducing the severity of the clinical symptoms and/or effects of the infection, and/or reducing the duration of the infection/symptoms/effects.

The vaccines comprise the mutant *E. chaffeensis* strain(s) described herein dispersed in a pharmaceutically-acceptable carrier. The term carrier is used herein to refer to diluents, excipients, vehicles, and the like, in which the mutant *E. chaffeensis* strain(s) may be dispersed for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the mutant *E. chaffeensis* strain(s) or other agents and to minimize any adverse side effects in the subject, as would be well known to one of skill in the art. Pharmaceutically-acceptable ingredients include those acceptable for veterinary use as well as human pharmaceutical use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), aqueous dextrose solutions, aqueous glycerol solutions, ethanol, normal allantoic fluid, various oil-in-water or water-in-oil emulsions, as well as dimethyl sulfoxide (DMSO) or other acceptable vehicles, and the like.

The vaccine can comprise a therapeutically effective amount of live attenuated mutant *E. chaffeensis* dispersed in the carrier. As used herein, a "therapeutically effective" amount refers to the amount that will elicit the biological or medical response of a tissue, system, or subject that is being sought by a researcher or clinician, and in particular elicit some desired protective effect as against the infection by priming or stimulating an immune response specific for one or more strains of *E. chaffeensis*. One of skill in the art recognizes that an amount may be considered therapeutically "effective" even if the condition is not totally eradicated or prevented, but it or its symptoms and/or effects are improved or alleviated partially in the subject. In some embodiments, the composition will comprise from about 5% to about 95% by weight of a mutant *E. chaffeensis* described herein, and preferably from about 30% to about 90% by weight of the mutant *E. chaffeensis*, based upon the total weight of the composition taken as 100% by weight. In some embodiments, combinations of more than one type of the described *E. chaffeensis* mutants can be included in the composition, in which case the total levels of all such mutant *E. chaffeensis* strains will preferably fall within the ranges described above. Such multi-valent vaccines are preferred for use in vaccination in some embodiments. In some embodiments, modifications may be made to the insertions, such as deletions of the antibiotic cassette or creation of new targeted insertions within the genes Ech_0660, Ech_0379, or Ech_0230 to improve the vaccine effectiveness. In some embodiments, similar mutations may be made in other *Ehrlichia* and *Anaplasma* species pathogens impacting the health of people and dogs upon their infections and they will be used similarly as vaccines.

Other ingredients may be included in the composition, such as adjuvants, other active agents, preservatives, buffering agents, salts, other pharmaceutically-acceptable ingredients, including residual amounts of ingredients used in vaccine manufacturing. The term "adjuvant" is used herein to refer to substances that have immunopotentiating effects and are added to or co-formulated in the vaccine composition in order to enhance, elicit, and/or modulate the innate, humoral, and/or cell-mediated immune response against the vaccine components. Suitable adjuvants include: aluminum salts, such as aluminum hydroxide, aluminum phosphate, alum (potassium aluminum sulfate), or mixed aluminum salts, peptides, oil or hydrocarbon emulsions, or any other adjuvant deemed suitable for human or animal use. In some embodiments, the vaccine is substantially free of any adjuvants, where the term "substantially free" means that the ingredient is not intentionally added or part of the composition, although it is recognized that residual or incidental amounts or impurities may be present in low amounts (e.g., less than about 0.1% by weight and preferably less than about 0.01% by weight, based upon the total weight of the composite taken as 100% by weight). Other active agents that could be included in the composition include antiviral compounds or any immunogenic active components (e.g., antigens) such as those that resemble a disease-causing microorganism or infectious agent, and/or are made from weakened or killed forms of the same, its toxins, subunits, particles, and/or one of its surface proteins, such that it provokes an immune response to that microorganism or infectious agent. In addition to live, modified, or attenuated vaccine components, active agents using recombinant or synthetic peptides/proteins, carbohydrates, or antigens can also be used, including those targeted to the gene products of Ech_0660, Ech_0379, and/or Ech_0230. Antibiotics can also be used as part of vaccine production and may be present in small amounts in the vaccine, such as neomycin, polymyxin B, streptomycin and gentamicin. In some embodiments, the vaccine composition is substantially free of any other active (immunogenic) agents, other than the mutant *E. chaffeensis* and optional adjuvant, dispersed in the carrier.

In use, the vaccine composition is administered to a subject. Various routes of administration can be used depending upon the particular carrier and other ingredients used. For example, the vaccine can be injected intramuscularly, subcutaneously, intradermally, or intravenously using a needle and syringe, or a needleless injection device. The vaccine can also be administered mucosally, such as intranasal administration. For intranasal administration, the vaccine composition is usually administered through the nasal passage as drops, large particle aerosol (greater than about 10 microns), or spray into the upper respiratory tract. While stimulation of a protective immune response with a single dose is preferred, additional dosages can be administered, by the same or different route, to achieve the desired prophylactic or therapeutic effect. The vaccine can also be administered using a prime and boost regime if deemed necessary. In some embodiments, the methods described herein are useful for preventing the occurrence or incidence of *Ehrlichia* infection and/or preventing the effects of *Anaplasma* infection, as described above.

In some embodiments, the vaccine can be provided in unit dosage form in a suitable container. The term "unit dosage form" refers to a physically discrete unit suitable as a unitary dosage for human or animal use. Each unit dosage form may contain a predetermined amount of the vaccine (and/or other active agents) in the carrier calculated to produce the desired effect. In other embodiments, the vaccine can be provided separate from the carrier (e.g., in its own vial, ampule, sachet, or other suitable container) for on-site mixing before administration to a subject. A kit comprising the vaccine is also disclosed herein. The kit further comprises instructions for administering the vaccine to a subject. The virus can be provided as part of a dosage unit, already dispersed in a pharmaceutically-acceptable carrier, or it can be provided separately from the carrier. The kit can further comprise instructions for preparing the virus for administration to a subject, including for example, instructions for dispersing the virus in a suitable carrier.

Advantageously, vaccination with live, attenuated mutant *E. chaffeensis* induces pathogen-specific humoral and cellular immunity, and protection from tick-transmitted *E. chaffeensis* infection in a physiologic host. In one or more embodiments, vaccination with live, attenuated mutant *E. chaffeensis* generates a host response that is protective against infection in both the reservoir host (deer) and in an incidental host (dogs). In one or more embodiments, vaccination is completely protective against infection (Ech_0660 mutation). In one or more embodiments, vaccination is at least partially protective against infection (Ech_0379 mutation). In some embodiments, the immunogenic composition comprises a mixture of mutated *E. chaffeensis* strains comprising at least a mutation in Ech_0660 in one strain and a mutation in Ech_0379 in a second strain.

In one or more embodiments, administering the immunogenic composition to a subject will result in reducing rickettsemia when the subject is exposed to *Ehrlichia*, and/or artificially challenged with a wild type infection. In one or more embodiments, administering the immunogenic composition to a subject will result in complete clearance of the pathogen from both reservoir and incidental hosts. In one or more embodiments, administering the immunogenic composition to a subject will result in a rise in *E. chaffeensis*-specific antibody titers in the subject. In one or more embodiments, administering the immunogenic composition to a subject will result in a significant Th1 response in peripheral blood of the subject as measured by *E. chaffeensis* antigen-dependent CD4+ T cell proliferation and IFNγ production. In one or more embodiments, administering the immunogenic composition to a subject will result in a significant IL-17 production by peripheral blood leukocytes in the subject. In one or more embodiments, administering the immunogenic composition to a subject will does not result a significant antigen-dependent CD8+ T cell response in the subject.

Using the methodology and technology described herein, different attenuated *Ehrlichia* and/or *Anaplasma* vaccines can be developed and used for canines, and other species including, but not limited to human, equine, cervus (deer), feline, goats, non-human primate, and the like. The methods can be also applied for clinical research and/or study. Thus, kits for study and/or generation of additional mutant *Ehrlichia* strains are also described herein. The kits comprise vectors (plasmids) as described herein encoding for the insertional mutations. The kit can also include vectors encoding for the target genes. Alternatively, such sequences can be determined by the end-user. The kit may include plasmids for subsequently inserting the insertional mutation sequences for generation of the mutant *Ehrlichia* strains. The kit may further include additional components, including cells, culture medium, buffers, along with instructions for their use to generate the mutant *Ehrlichia* strains.

The methods can also be applied towards developing drugs targeting the gene products of genes Ech_0660, Ech_0379, and Ech_0230, and their homologs of other related rickettsial pathogens to inhibit or reduce the effects, severity, or symptoms of *Ehrlichia* or *Anaplasma* infections.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Introduction

Figure 11A:
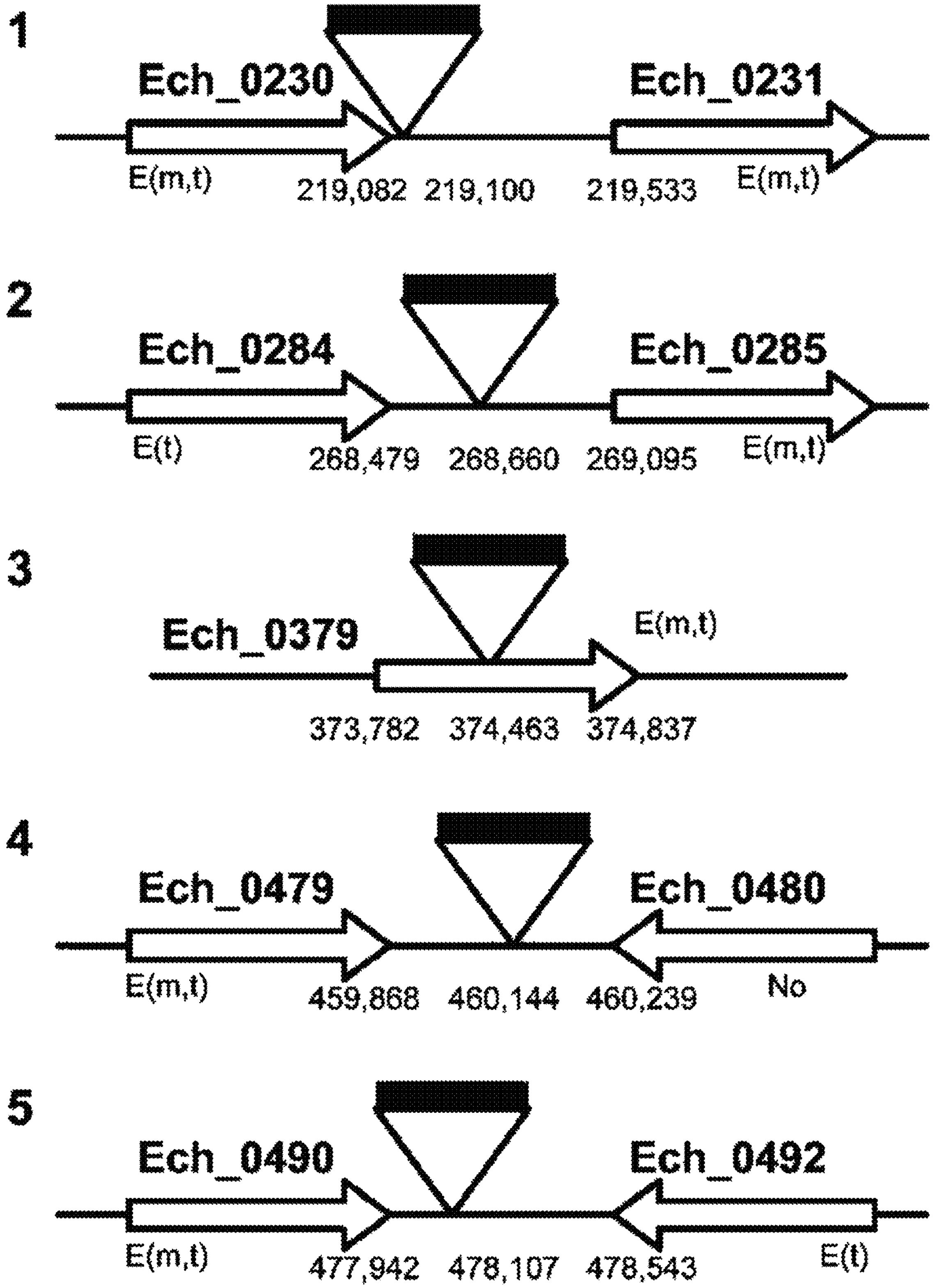
FIG. 11A is an illustration of genomic locations for transposon mutation in *E. chaffeensis*.
Figure 11B:
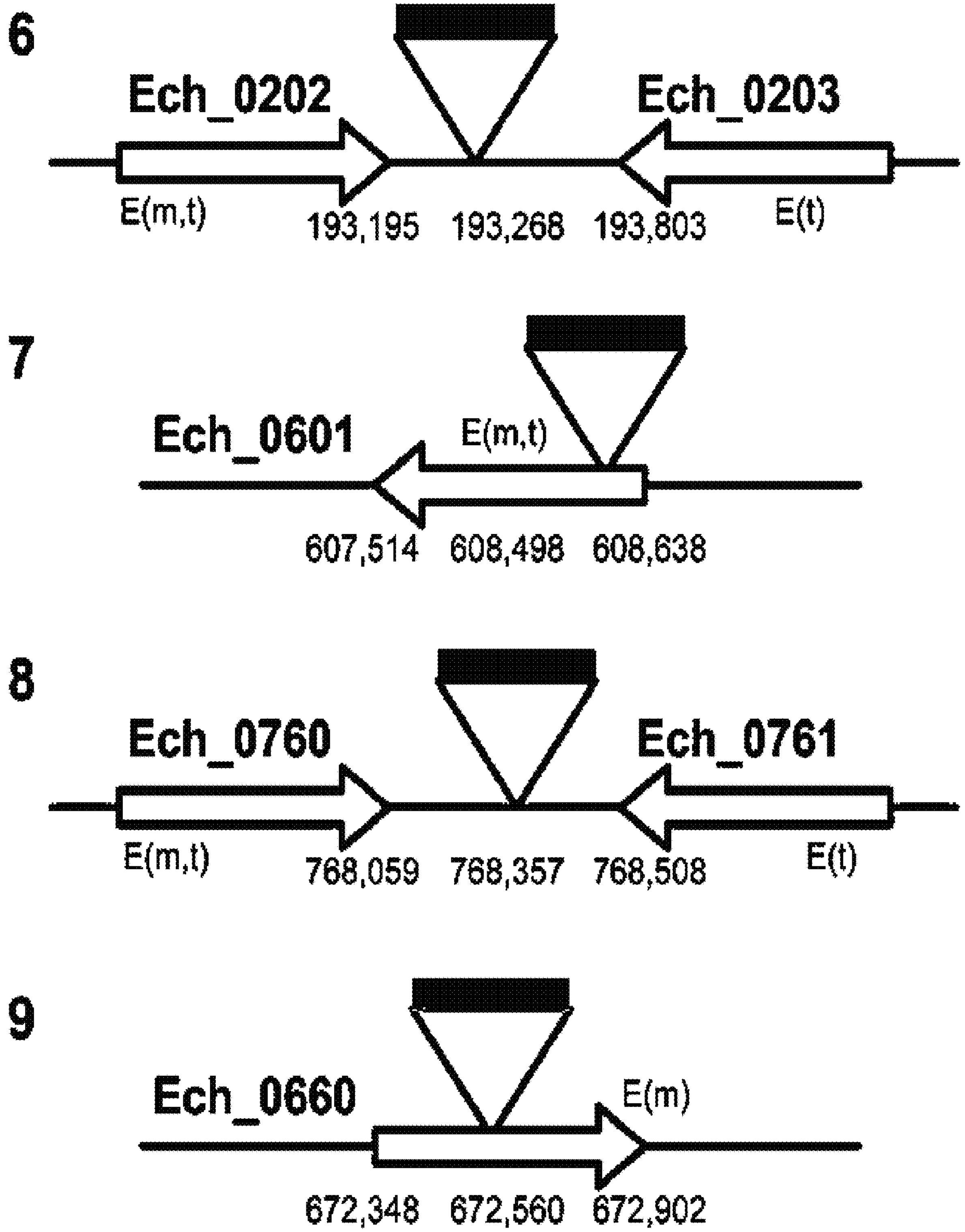
FIG. 11B is an illustration of genomic locations for transposon mutation in *E. chaffeensis.*

In a recent study, we described nine transposon insertion mutations in *E. chaffeensis* (Cheng et al., Targeted and Random Mutagenesis of *Ehrlichia chaffeensis* for the Identification of Genes Required for In vivo Infection PLOS Pathogens, Vol. 9, Iss. 2 (2013), incorporated by reference herein) (see FIG. 11). Genomic locations of the insertion sites and the genes at or near the insertions, as per the whole genome data (GenBank # CP000236.1) are shown in FIG. 11. *E. chaffeensis* genomic DNAs from three independent transformations with mCherry (one transformation) and GFPuv (two transformations) Himarl transposon plasmids were used to determine the integration locations by inverse PCRs and ST-PCRs followed by DNA sequence analysis. Genomic locations of the insertion sites and the genes at or near the insertions were presented. The gene expression data assessed by RT-PCR are also included in the figure (E, expressed gene; m, in macrophage culture; t, in tick cell culture; No, gene not expressed). The insertions in mCherry transformants are shown on the left, and insertions in GFPuv transformants are depicted on the right. Numbers 6-8 are the first GFPuv transformants, and number 10 is the second GFPuv transformant).

In the current study, we investigated the impact of the insertion mutations in the pathogen's growth in an incidental host, tick and in altering transcriptional activities of genes near to the insertion sites. The potential of attenuated mutants to confer protection against infection challenge was also investigated. We present the first evidence that transposon mutations in *E. chaffeensis* cause polar effects in impacting gene expression from the nearby genes, in addition to disrupting gene functions for mutations existing within a gene. Further, we report that the transposon insertion mutation within the Ech_0660 gene causes attenuation and offers protection against infection challenges in both deer and dogs.

The *E. chaffeensis* Arkansas isolate (wild type and the mutants) and *E. canis* Oklahoma strain were continuously cultivated in the macrophage like cell line (DH82) for use in examples described below. Animal experiments with deer and dogs were performed by complying with the Public Health Service (PHS) Policy on the Humane Care and Use of Laboratory Animals, the US Department of Agriculture's (USDA) Animal Welfare Act & Regulations (9CFR Chapter 1, 2.31), and with approvals of the Oklahoma State University (OSU) and Kansas State University (KSU) Institutional Animal Care and Use Committees (IACUC), and as per the guidelines of the protocols. Laboratory-reared deer and pure-bred laboratory-reared dogs were used for conducting infection experiments. Purebred beagle dogs of 5-6 months of age of either sex were obtained from Covance Research Products (Denver, Pa.). Infection experiments were done according to established protocols.

The quantitative IgG ELISA data were analyzed using the 2-tailed unpaired Student t test (GraphPad software, graphpad.com, La Jolla, Calif.). Statistical significance was set for differences between the experimental groups at $P \leq 0.05$. To maximize power to detect differences, T cell and antibody responses were compared using an analysis of variance accounting for the repeated measures on animals over time and the nesting of animals within each infection group was performed as previously described. For cytokine assays, ELISA results on cell culture supernatants from day 7-post infection were analyzed using a 1-way ANOVA with Bonferri post-test analysis.

Example 1 illustrates the clonal purification and verification of *E. chaffeensis* mutants. Example 2 illustrates the impact of mutations on the transcriptional activities of genes near the insertion sites by RT-PCR analysis. Example 3 illustrates the infection of animals with strains of mutant or wild type *E. chaffeensis* and the impact of these mutations on *E. chaffeensis* growth in an incidental host. Example 4 illustrates the needle infection of *A. americanum* ticks with mutants or wild type *E. chaffeensis* cultures. Example 5 illustrates the antibody, CD8+, and CD4+ T Cell responses to vaccination and challenge. Example 6 illustrates that attenuated mutants confer protection against wild type infection challenge in deer and dogs Example 1

Clonal Purification and Verification of *E. chaffeensis* Mutants

Transposon mutants of *E. chaffeensis* were clonally purified by limiting dilution Briefly, host cell-free *E. chaffeensis* mutant pools were prepared, the numbers of organisms were estimated using a hemocytometer, and diluted to generate about one infected cell to be transferred per chamber in a 48-well plate containing confluent DH82 cells and incubated at 37° C. When the infectivity reached to ~80%, 0.7 ml culture from each well was harvested for genomic DNA isolation. The remaining culture was transferred to a T25 flask containing confluent DH82 cells for expanding the culture growth. Clonal purity of mutants was assessed by PCR targeting to each insertion region and by performing Southern blot analysis with genomic DNA digested with Bgl II and hybridized with insertion-specific spectinomycin (aad) probe. Blots were assessed for the presence of single predicted DNA fragments for each clonal mutant.

To characterize the mutant organisms, we clonally purified five mutants by limiting dilution technique; Ech_0202, Ech_0284, Ech_0379, Ech_0480, and Ech_0660; clonal purity of mutants was verified by Southern blot analysis (FIG. 1). Expected genomic DNA fragments for the Bgl II restriction endonuclease digestion, estimated from the position of transposon insertions, were calculated (FIG. 1A) and observed in DNA of each purified mutant as illustrated by agarose gel electrophoresis (FIG. 1B). Lanes 1-5 represent the mutants Ech_0202, Ech_0284, Ech_0379, Ech_0480 and Ech_0660, respectively.

Example 2

Impact of Mutations on the Transcriptional Activities of Genes Near the Insertion Sites by RT-PCR Analysis Total RNA, free of contaminated genomic DNA, was isolated as according to standard protocols. RNA concentrations from wild type and clonal mutants were equalized and semi-quantitative RT-PCR targeting *E chaffeensis* genes surrounding the transposon insertion sites was performed by 35 cycles of amplification using the gene specific primer sets described in Table 1.

TABLE 1

Primers used for RT-PCR of genes surrounding the insertion sites

| Primer name | Gene target | Amplicon size (bp) | Primer sequence |
|---|---|---|---|
| RRG1382 | Ech_0202 | 314 | 5'-ttg ctg ata gtg tgg cag ctg aag (SEQ ID NO: 13) |
| RRG1383 | | | 5'-tct cca tct tgg ata aca gca gg (SEQ ID NO: 14) |
| RRG1384 | Ech_0203 | 175 | 5'-tgt gtc ctg ttg tta tgg gtt ctc (SEQ ID NO: 15) |
| RRG1385 | | | 5'-tcc cta agt aat atg gaa cca tct gca c (SEQ ID NO: 16) |
| RRG1370 | Ech_0284 | 380 | 5'-tct gct aga agt gct act cta gg (SEQ ID NO: 17) |
| RRG1371 | | | 5'-tcc cac agt gta gct ctc tgc (SEQ ID NO: 18) |
| RRG1372 | Ech_0285 | 417 | 5'-atg act gct gcc att aca gtt ggg (SEQ ID NO: 19) |
| RRG1373 | | | 5'-cct cat cac ttg ttc ctc ctt c (SEQ ID NO: 20) |
| RRG1632 | Ech_0378 | 446 | 5'-tgc tat agg gat acc tgt agc ttt tgc (SEQ ID NO: 21) |
| RRG1633 | | | 5'-gca aga cca tcg tac gta cta ggt g (SEQ ID NO: 22) |
| RRG1276 | Ech_0379 | 373 | 5'-cta agg ttg tag gga atg caa cc (SEQ ID NO: 23) |
| RRG1277 | | | 5'-aca agg taa gta cct tgc ttg ctc (SEQ ID NO: 24) |
| RRG1634 | Ech_0380 | 161 | 5'-atg tgc tct gta tca att gct tg (SEQ ID NO: 25) |
| RRG1635 | | | 5'-aac aaa gaa gta aaa aga cat aca tg (SEQ ID NO: 26) |
| RRG1374 | Ech_0479 | 357 | 5'-act cct tgg caa tgg tgt gta g (SEQ ID NO: 27) |
| RRG1375 | | | 5'-aat cgc tct aga caa cac tga agg (SEQ ID NO: 28) |

TABLE 1-continued

Primers used for RT-PCR of genes surrounding the insertion sites

| Primer name | Gene target | Amplicon size (bp) | Primer sequence |
|---|---|---|---|
| RRG1376 | Ech_0480 | 368 | 5'-tat gta act tct ttg cct ctt atg (SEQ ID NO: 29) |
| RRG1377 | | | 5'-atg aaa tct tta gtg act cga cc (SEQ ID NO: 30) |
| RRG1636 | Ech_0659 | 224 | 5'-act aga tga att tga cta tac aat tga tg (SEQ ID NO: 31) |
| RRG1637 | | | 5'-ttt aag ctt tgt aag ctg tta gaa t (SEQ ID NO: 32) |
| RRG1344 | Ech_0660 | 265 | 5'-tgt acc tgt atc ctc acc tat cac c (SEQ ID NO: 33) |
| RRG1345 | | | 5'-cta tca att ctt cac ttc cat ttg tgt g (SEQ ID NO: 34) |
| RRG1638 | Ech_0661 | 155 | 5'-atc tac tgc tac caa ccc aat ac (SEQ ID NO: 35) |
| RRG1639 | | | 5'-tag tgc ata tgc aat ttc att gtg c (SEQ ID NO: 36) |

Insertional mutations within Ech_0230, Ech_0379 and Ech_0660 caused transcriptional inactivation from these genes. To assess the polar effects in altering transcriptional activities of genes surrounding the insertions, we evaluated transcription from genes located immediately upstream and downstream to insertion sites for the five clonally purified mutants (FIG. 2). Total RNA isolated from wild-type *E. chaffeensis* (lane 1) and clonal mutants (lane 2) was assessed for the genes 5' and 3' to insertion sites by semi quantitative RT-PCR. FIGS. 2A-2D have the cartoons depicting the insertions within the genome and the genes near the insertions 111, along with corresponding RT-PCR products resolved on agarose gels for each of the respective genes. No template controls (lane 3) and wild type genomic DNA template reactions (lane 4) were included to serve as negative and positive controls, respectively for each reaction. M represents 1 kb plus DNA ladder (Life Technologies Inc. Carlsbad, Calif.). With exception of the intergenic mutation downstream to Ech_0202, all other mutations influenced the transcript levels from the genes immediately upstream and/or downstream to the insertion sites. The insertion 3' to Ech_0284 caused an enhancement of gene expression from the Ech_0285 gene. Similarly, mutation within Ech_0379 caused decline of the transcription to undetectable levels from the upstream gene, Ech_0378, similar to the loss of transcription from Ech_0379 gene previously published, while not impacting the transcript level for the downstream gene, Ech_0380. The mutation 3' to Ech_0479 enhanced transcription from this gene and also activated the transcriptionally silent gene, Ech_0480. Mutation within Ech_0660 resulted in the decline in transcription to undetectable level from Ech_0659, similar to transcript knockdown from Ech_0660 gene. This mutation had no impact on the transcript level of Ech_0661.

Example 3

Infection of Animals with Strains of Mutant or Wild Type *E. chaffeensis* and the Impact of these Mutations on *E. chaffeensis* Growth in an Incidental Host Animals were injected with transposon mutants as a pool, clonally purified organisms, or with wild type *E. chaffeensis*. Inocula were prepared and inoculated with an estimated concentration of $\sim 2 \times 10^8$ *Ehrlichia* organisms in 1 ml. The presence of mutants and wild type organisms in an animal was assessed in blood drawn several days post infection by performing culture recovery or by nested PCR analysis.

TABLE 2

Verification of the *E. chaffeensis* infection status by nested PCR targeting to the transposon insertion sites in mutant pool infected dog blood #

| | | Days post infection | | | | | | | | | | | | |
|---|---|---|---|---|---|---|---|---|---|---|---|---|---|---|
| | Insertion site | 0 | 2 | 5 | 7 | 9 | 12 | 14 | 16 | 19 | 21 | 29 | 35 | 44 |
| Dog 1 | Ech_0202 | – | – | – | – | – | – | – | – | – | – | – | – | – |
| | Ech_0230 | – | – | – | – | – | – | – | – | – | – | – | – | – |
| | Ech_0379 | – | – | – | – | – | – | – | – | – | – | – | – | – |
| | Ech_0480 | – | + | + | + | + | + | – | + | – | – | + | + | + |
| | Ech_0490 | – | – | – | – | – | – | + | + | + | – | + | – | – |
| | Ech_0601 | – | – | – | – | – | – | – | – | – | – | – | – | + |
| | Ech_0660 | – | – | – | – | – | – | – | – | – | – | – | – | – |
| | Ech_0760 | – | – | – | – | – | – | + | – | – | – | + | – | – |
| Dog 2 | Ech_0202 | – | – | – | – | – | – | – | – | – | – | – | – | – |
| | Ech_0230 | – | – | – | – | – | – | – | – | – | – | – | – | – |
| | Ech_0379 | – | – | – | – | – | – | – | – | – | – | – | – | – |
| | Ech_0480 | – | + | + | + | – | – | + | – | – | – | + | + | + |

TABLE 2-continued

Verification of the *E. chaffeensis* infection status by nested PCR targeting to the transposon insertion sites in mutant pool infected dog blood #

| | | Days post infection | | | | | | | | | | | | |
|---|---|---|---|---|---|---|---|---|---|---|---|---|---|---|
| | Insertion site | 0 | 2 | 5 | 7 | 9 | 12 | 14 | 16 | 19 | 21 | 29 | 35 | 44 |
| | Ech_0490 | − | + | − | − | − | − | − | − | − | − | − | − | − |
| | Ech_0601 | − | − | − | − | + | − | − | − | − | − | − | − | − |
| | Ech_0660 | − | − | − | − | − | − | − | − | − | − | − | − | − |
| | Ech_0760 | − | − | − | − | − | − | − | − | − | − | − | + | + |
| Dog 3 | Ech_0284 | − | − | − | − | − | − | + | + | + | + | + | − | + |

The signs − and + refer to samples tested negative or positive by culture recovery and/or nested PCR, respectively.

*E. chaffeensis* transposon mutants grew well under in vitro culture conditions, while their growth and persistence in the reservoir host, white-tailed deer, was variable; insertions causing transcriptional inactivation from three putative membrane protein encoding genes Ech_0230, Ech_0379 and Ech_0660 resulted in the attenuated growth in deer. To examine if the mutations similarly impacted the pathogen's growth in an incidental host, we conducted experimental infection studies in three dogs. Infection progression in the dogs was followed for 44 days by sampling blood once every 2-7 day intervals. The dogs tested positive for the mutants similar to our prior observations in deer when assessed by culture recovery and/or insertion-specific PCRs at various time points post infections (Table 2). As in deer, dogs tested negative for the same three insertion mutations at Ech_0230, Ech_0379 and Ech_0660 genes. In addition, the mutant near Ech_0202 gene was undetectable. Evaluation Ech_0202, Ech_0601 and Ech_0760 mutants in vivo was assessed for the first time. Ech_0601 is an intragenic mutation, while Ech_0202 and Ech_0760 mutations are intergenic mutations downstream from the coding sequences of Ech_0202 and Ech_0760 genes, respectively. As the mutants' progression in dogs is similar to deer for the previously assessed six mutants, we reasoned that the infection progression with Ech_0202, Ech_0601 and Ech_0760 mutants in deer will also be similar to dogs. We followed infection for two months in a deer with a pool of these three mutants (Table 3). As in dogs, Ech_0202 mutant was undetectable in deer, while Ech_0601 and Ech_0760 mutants persisted.

Mutants with attenuated growth in vertebrate host species were considered vaccine candidates.

TABLE 3

Infection status in deer blood with mutant pool containing Ech_0202, Ech_0601 and Ech_0760#

| | Days post infection | | | | | | | | | | | | | | | | | |
|---|---|---|---|---|---|---|---|---|---|---|---|---|---|---|---|---|---|---|
| Insertion site | 0 | 5 | 6 | 8 | 10 | 14 | 18 | 21 | 28 | 32 | 35 | 39 | 42 | 46 | 49 | 52 | 59 | 63 |
| Ech_0202 | − | − | − | − | − | − | − | − | − | − | − | − | − | − | − | − | − | − |
| Ech_0601 | − | − | + | − | − | + | + | + | + | − | − | − | − | − | − | − | − | + |
| Ech_0760 | − | + | − | − | + | − | + | + | − | − | − | − | − | − | − | − | − | − |

#The signs − and + refer to samples tested negative or positive by culture recovery and/or nested PCR, respectively.

Example 4

Needle Infection of *A. americanum* Ticks with Mutants or Wild Type *E. chaffeensis* Cultures for Assessing the Impact of Mutations on *E. chaffeensis* Growth in the Tick Vector

*A. americanum* nymphal ticks experimentally fed and dropped after completing a blood meal from a naïve sheep were used in this study. Fed nymphs were purchased from the Oklahoma State University tick facility. Within 24-48 h post blood meal, nymphs were injected with about 5 μl of 10 fold concentrated cultured *E. chaffeensis* (mutants or wild type). Briefly, culture in PBS was used for needle puncture inoculation into the ventral side of ticks. Ticks were allowed to molt to adults at room temperature. Total genomic DNA from ticks was individually isolated, resuspended into 100 μl of nuclease-free water and 2 μl each of the DNA was used as template for PCR analysis. The presence of *E. chaffeensis* (wild type or mutant organisms) was determined by nested PCR assays as described in Example 1 above.

Infection of *A. americanum* ticks by needle inoculation method with *E. chaffeensis* mutants demonstrated that the mutated genes were essential only for survival in the vertebrate host but not for the organism's persistence in its tick vector. Four groups of engorged nymphal ticks were included in this experiment; group 1 received wild-type *E. chaffeensis*, group 2 received a pool of five mutants grown together (Ech_0230, Ech_0284, Ech_0379, Ech_0480 and Ech_0490), group 3 received an equal mixture of five individually cultured mutants (Ech_0202, Ech_0284, Ech_0379, Ech_0480 and Ech_0660) and group 4 contained five sub-groups inoculated with mutants individually cultured (the same five mutants used in group 3 experiment). Following molting of nymphs to adults, total genomic DNA was recovered from randomly selected ticks of both sexes from each group (14-21 ticks per group/subgroup) and assessed for infection rates by wild type or mutant-specific nested PCR assays, data summarized in Table 4. Infection with wild type *E. chaffeensis* (group 1) was 9.5%. Infection rates with the mutants were variable for each mutant in groups 2-4. The highest infection rate was observed for Ech_0480 mutant and its infection rates were very similar in all three groups of ticks at 50-57%. The Ech_0379 mutant infection in groups 2-4 was also very similar at 28-30%. Ech_0202 infection was undetectable in a pool containing equal mixture (group 3); however, it was detected in one tick in the subgroup of group 4 receiving the mutant alone as the inoculum. These results illustrate the unexpected result that, contrary to the attenuated growth in deer and dogs, Ech_0230, Ech_0379 and Ech_0660 mutants showed no survival disadvantage in ticks.

TABLE 4

Infection rate of needle injected *A. americanum* ticks

| | Group 1 (wild type) | Group 2 (mutant pool) | Group 3 (equal mixture of mutants) | Group 4 (individual mutants) |
|---|---|---|---|---|
| wild type | 9.5% (2/21) | | | |
| Ech_0202 | | | 0% (0/14) | 4.7% (1/21) |
| Ech_0230 | | 20% (4/20) | | |
| Ech_0284 | | 5% (1/20) | 57.1% (8/14) | 23.8% (5/21) |
| Ech_0379 | | 30% (6/20) | 28.5% (4/14) | 28.5% (6/21) |
| Ech_0480 | | 50% (10/20) | 57.1% (8/14) | 57.1% (12/21) |
| Ech_0490 | | 50% (10/20) | | |
| Ech_0660 | | | 7.1% (1/14) | 23.8% (5/21) |

Example 5

Antibody, CD8+, and CD4+ T Cell Responses to Vaccination and Challenge

PBMCs were isolated by density centrifugation from buffy coat fractions of peripheral blood collected into 2× acid citrate dextrose. Cells were washed and resuspended in complete RPMI composed of RPMI-1640 (Gibco, Carlsbad, Calif.) supplemented with 2 mM L-glutamine, 25 mM HEPES buffer, 1% antibiotic-antimycotic solution, 50 mg/mL gentamicin sulfate, 1% nonessential amino acids, 2% essential amino acids, 1% sodium pyruvate, 50 μM 2-mercaptoethanol, and 10% (v/v) fetal bovine serum. For lymphocyte proliferation assays, cells were labeled with 1 μM CellTrace Violet (Life Technologies Inc.) per manufacturer's instructions. Cells were cultured for 5 days at 37° C. with $4\times10^5$ cells/well in 96-well plates and were stimulated with 10 μg/mL host cell-free *E. chaffeensis* whole-cell lysate that was grown in ISE6 tick cells. As a positive control, cells were stimulated with 5 μg/mL Concanavalin A (Sigma-Aldrich). For proliferation and intracellular cytokine staining data, background (mock) responses were subtracted from the response to antigen and results are presented as change over mock.

For surface staining of cells for flow cytometry, cells were resuspended at $10^7$ cells/mL in FACS buffer (0.1% $NaN_3$, 10% fetal calf serum, PBS) and incubated for 20 minutes at 4° C. with 10 μg/mL primary antibodies or as recommended by the manufacturer (mouse anti-canine CD3-FITC (clone CA17.2112), CD4-RPE or APC (clone YKIX302.9), CD8 RPE or APC (YCATE55.9) all from AbD Serotec (Raleigh, N.C.)). Cells were washed and fixed in BD FACS Lysis buffer (BD Biosciences).

Flow cytometry data were collected on a BD LSR Fortessa X-20 flow cytometer and analyzed using FlowJo software (Tree Star Inc., San Carlos, Calif.). Antigen-dependent $CD4^+$ T cells were identified based upon proliferation in response to *E. chaffeensis* antigen as determined by dilution of the Cell Trace Violet dye.

Figure 3A:
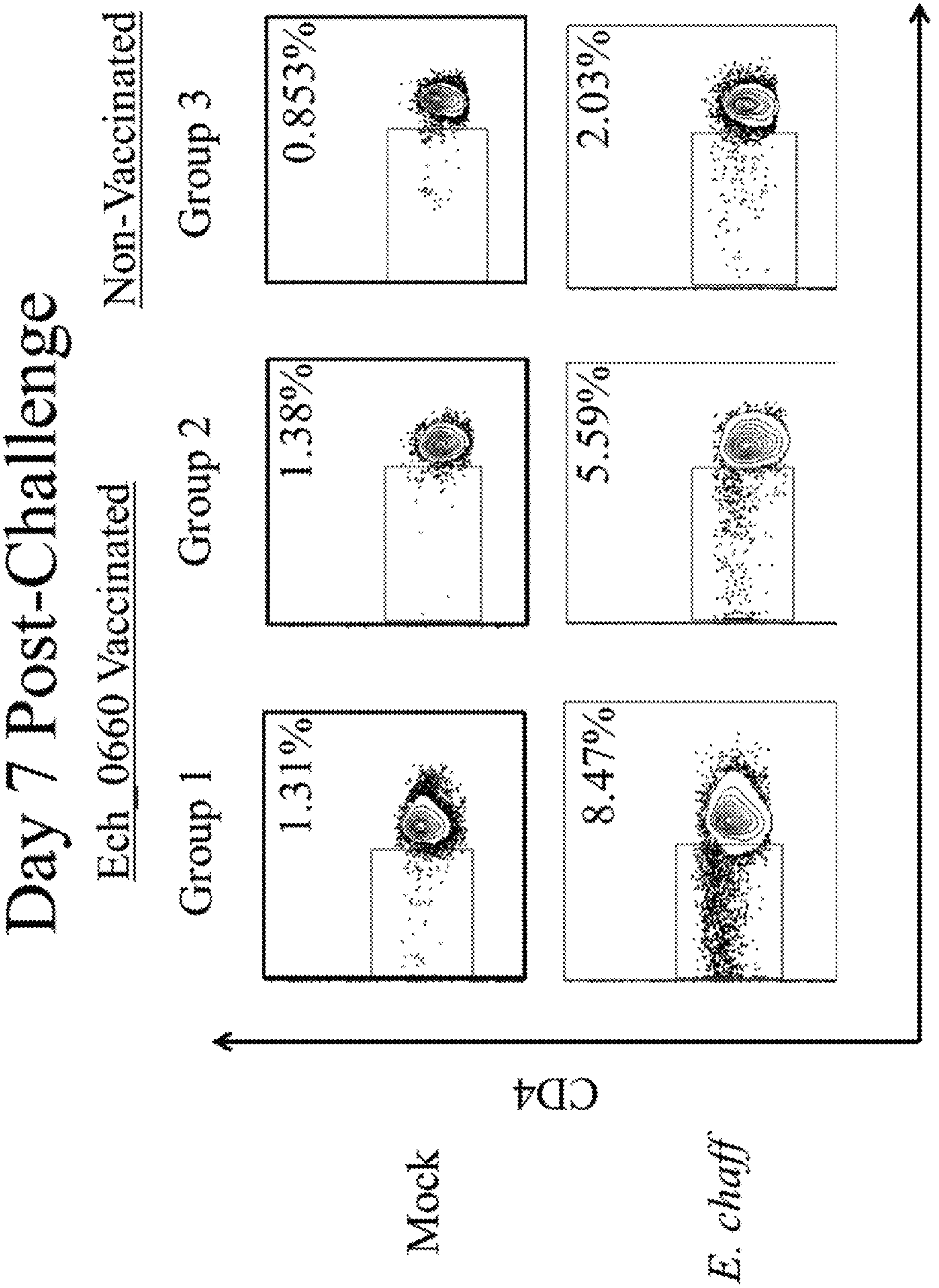
FIG. 3A shows representative Cell Trace Violet dilution profiles, gated on total live cells and total $CD3^+$ $CD4^+$ T cells.
Figure 3B:
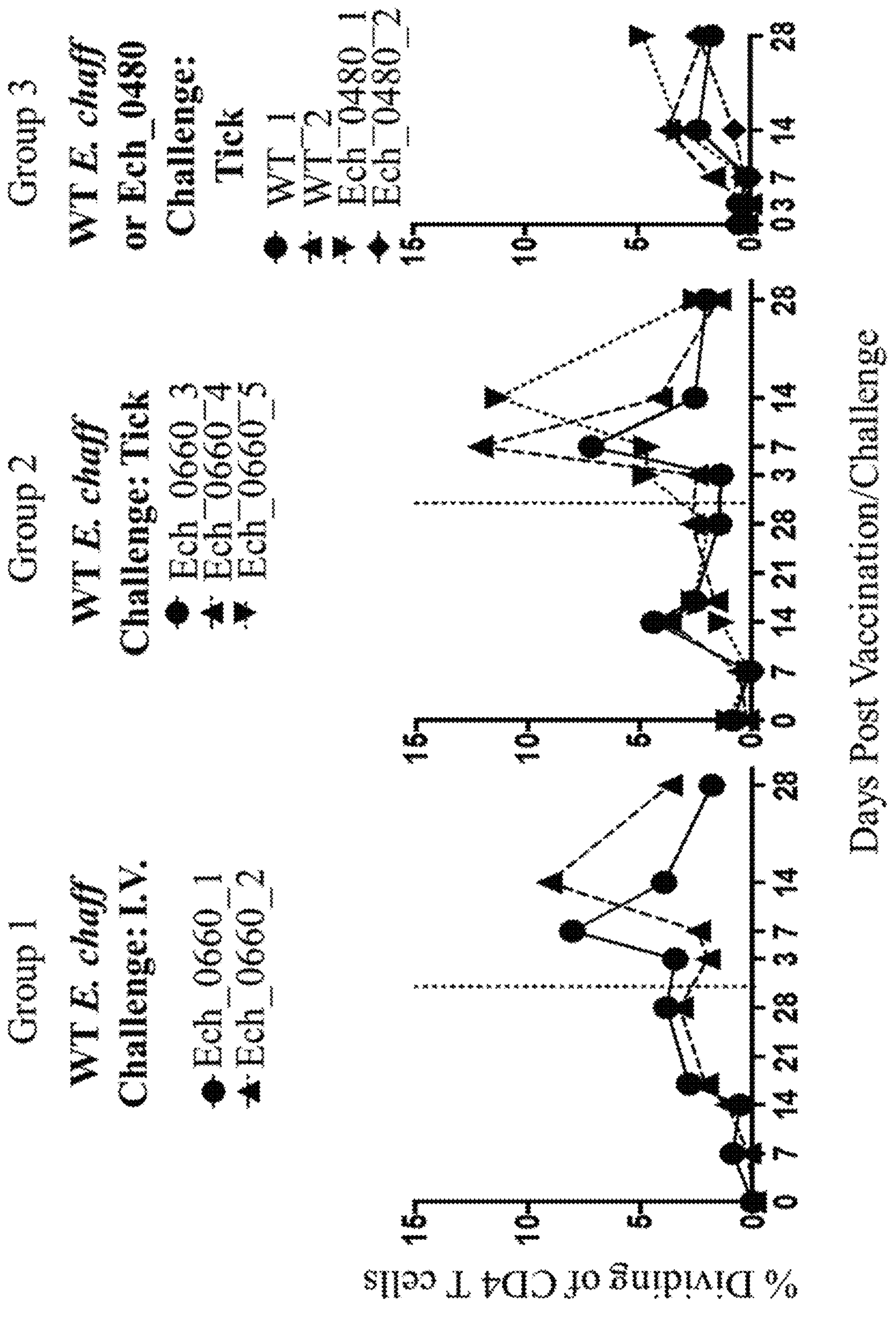
FIG. 3B shows the percentage of $CD4^+$ T cells that have proliferated in response to *E. chaffeensis* antigens as measured over the course of the experiment. Each line is representative of a single animal.

We next measured *E. chaffeensis*-specific $CD4^+$ T cell recall responses in peripheral blood from vaccinated and control dogs. PBMC were labeled with Cell Trace Violet, stimulated with host cell-free *E. chaffeensis* whole cell lysate and then analyzed by flow cytometry. Antigen-dependent $CD4^+$ T cells were identified based upon proliferation in response to *E. chaffeensis* antigen as determined by dilution of the Cell Trace Violet dye. Data in FIGS. 3A and 3B represent PBMC from dogs vaccinated with Ech_0660 and challenged with wild-type *E. chaffeensis* via needle inoculation (group 1, left panels), vaccinated with Ech_0660 and challenged with wild-type *E. chaffeensis* via tick inoculation (group 2, middle panels), or unvaccinated and infected with wild-type *E. chaffeensis* or Ech_0480 via tick inoculation (group 3, right panels) were labeled with Cell Trace Violet, then cultured for 5 days at $4\times10^6$ cells/mL in the presence or absence of 10 ug/mL *E. chaffeensis* host-cell free lysate grown in the tick ISE6 cell line. On day 5, $CD4^+$ T cells were analyzed by flow cytometry for Cell Trace Violet dilution as a measure of proliferation. FIG. 3A shows representative dilution profiles of mock and antigen-stimulated $CD4^+$ T cells from one representative animal per group on day 7 post-secondary challenge. The numbers depicted in FIG. 3A represent the percent of proliferating $CD3^+CD4^+$ cells contained within each gate. FIG. 3B shows the percentage of $CD4^+$ T cells dividing in response to antigen that was measured in all animals over the course of the experiment. Background levels of proliferation were subtracted from these values and results represent change in proliferation over mock stimulated cultures.

We observed an increase in the percentage of $CD4^+$ T cells that divided in response to *E. chaffeensis* antigen in PBMC collected on day 14-17 post inoculation with the Ech_0660 mutant. This percentage was further increased on day 7-14 following wild type *E. chaffeensis* challenge, consistent with a recall response. Vaccinated animals displayed significantly higher percentages of proliferating *E. chaffeensis* antigen-dependent $CD4^+$ T cells compared to unvaccinated dogs (FIG. 3B, $p=0.0081$).

We also measured antigen-dependent IFNγ production by $CD4^+$ T cells in the blood using intracellular cytokine staining. Protocol for harvest and surface staining was performed as described above with the addition of mouse-anti-bovine IFNγ-RPE (clone CC302) also from AbD Serotec (Raleigh, N.C.). The bovine IFNγ-specific clone CC302 has been previously demonstrated to cross-react with canine IFNγ. Intracellular cytokine staining for IFNγ was carried out using the BD Fixation and Permeabilization Solution kit (BD Biosciences). Cells were cultured with antigen for 5 days, and then Brefeldin A was added for the last 5-6 hours of incubation. Cells were surface stained and then fixed, permeabilized and stained for intracellular IFNγ (Clone CC302, 10 μg/mL) per manufacturer's instructions.

Figure 4A:
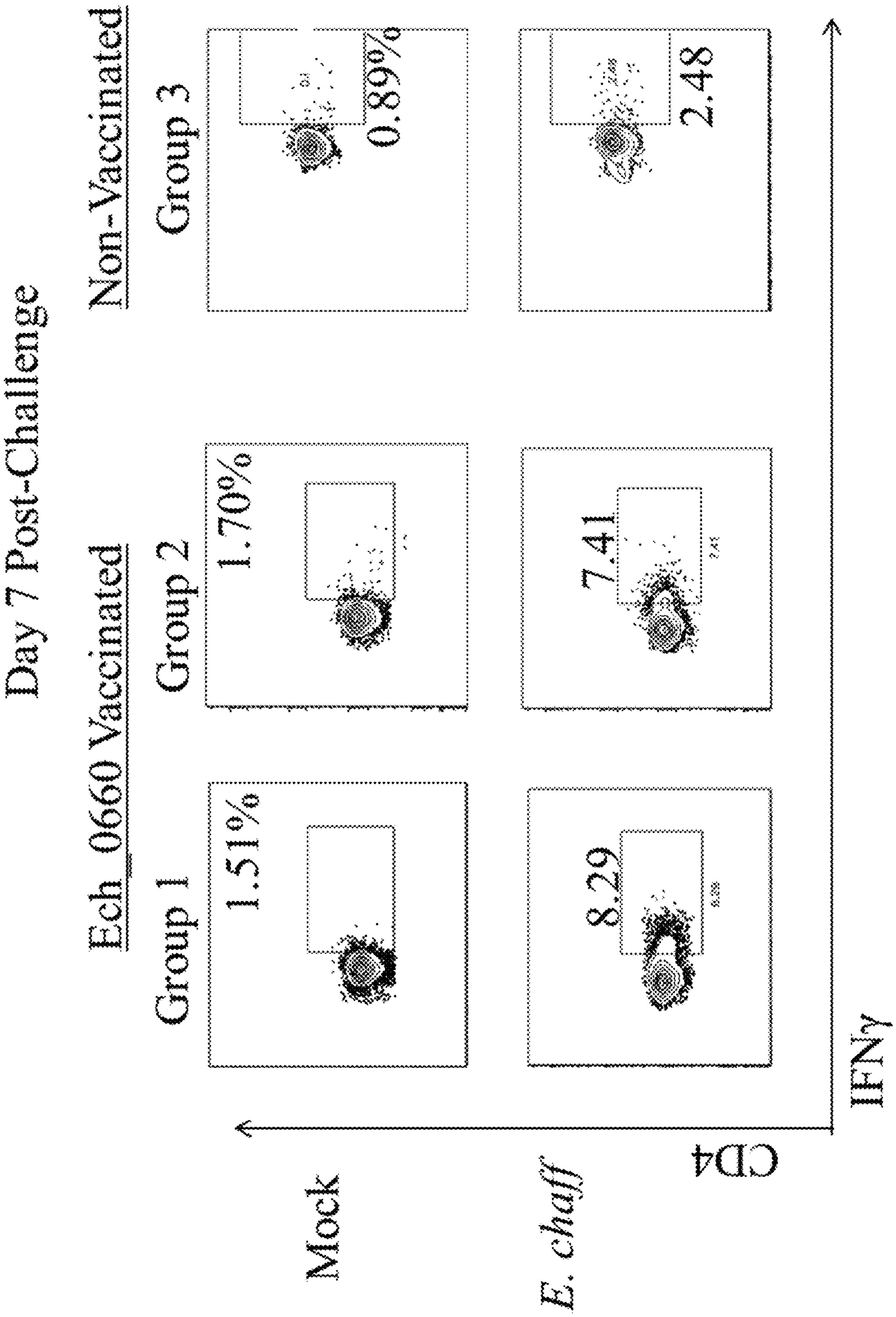
FIG. 4A shows representative flow plots of mock and antigen-stimulated $CD4^+$ T cells gated on $IFN\gamma^+$ cells from animals in groups 1, 2 and 3, gated on total live cells and total $CD3^+CD4^+$ T cells.
Figure 4B:
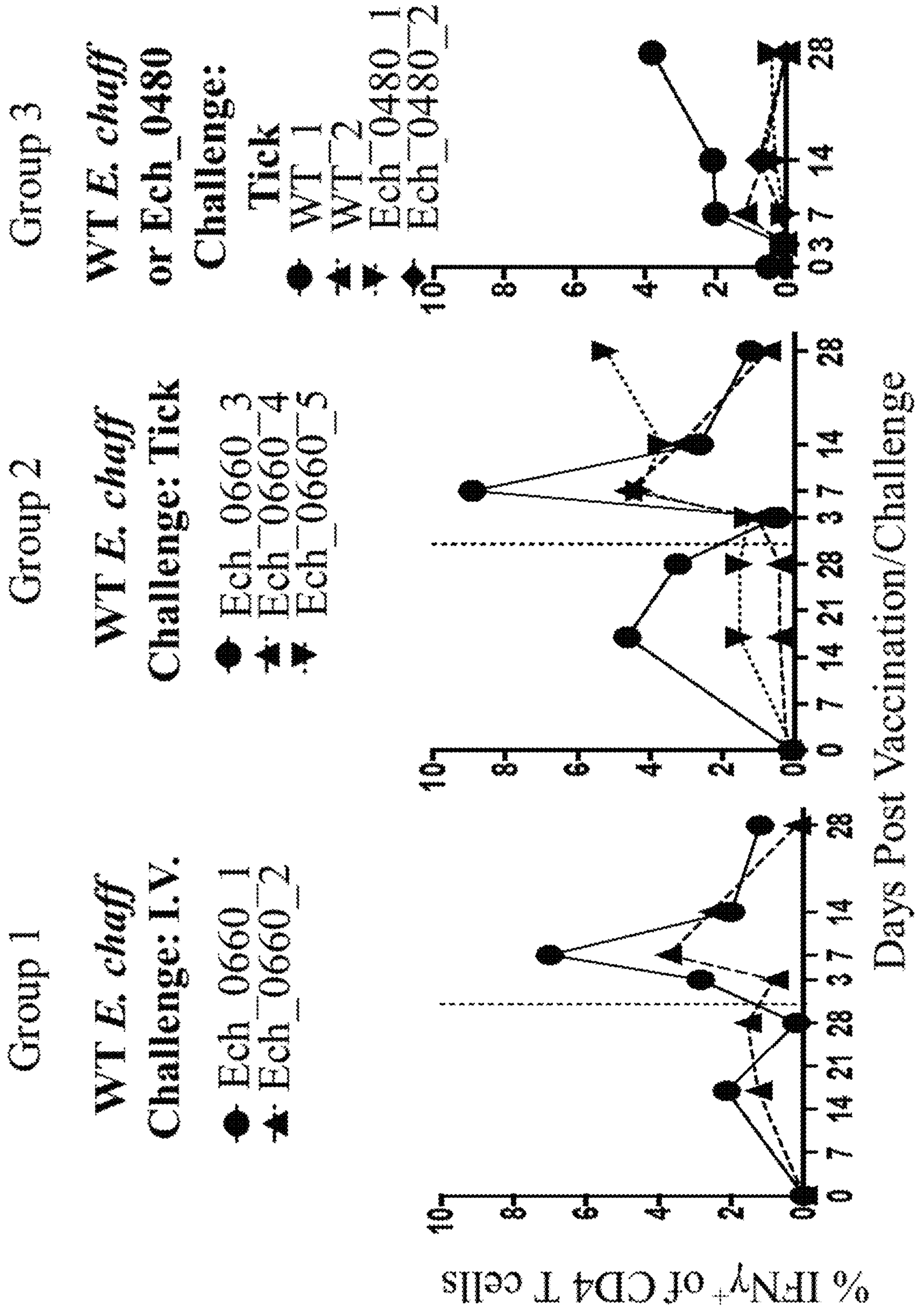
FIG. 4B shows the percentage of $IFN\gamma^+$ cells of total $CD4^+$ T cells in the blood.

FIG. 4 presents PBMC from dogs vaccinated with the Ech_0660 mutant and challenged with wild-type *E. chaffeensis* (groups 1-3, as in FIG. 2) were cultured for 5 days at $4\times10^6$ cells/mL in the presence or absence of 10 ug/mL *E. chaffeensis* host-cell free lysate grown in the tick ISE6 cell line. On day 5, brefeldin A was added for the last 6 hours of culture. $CD4^+$ T cells were stained for intracellular expression of IFNγ and analyzed by flow cytometry. FIG. 4A shows representative flow plots of mock and antigen-stimulated $CD4^+$ T cells gated on $IFN\gamma^+$ cells from animals in groups 1, 2 and 3, gated on total live cells and total $CD3^+CD4^+$ T cells. FIG. 4B shows the percentage of $IFN\gamma^+$ cells of total $CD4^+$ T cells in the blood measured over the course of the experiment. Background was subtracted from mock stimulated samples as above. We observed significantly increased percentages of $CD4^+$ T cells producing IFNγ in response to *E. chaffeensis* antigen in samples from vaccinated animals, compared to unvaccinated controls (FIG. 4B, $p=0.0025$).

Figure 5A:
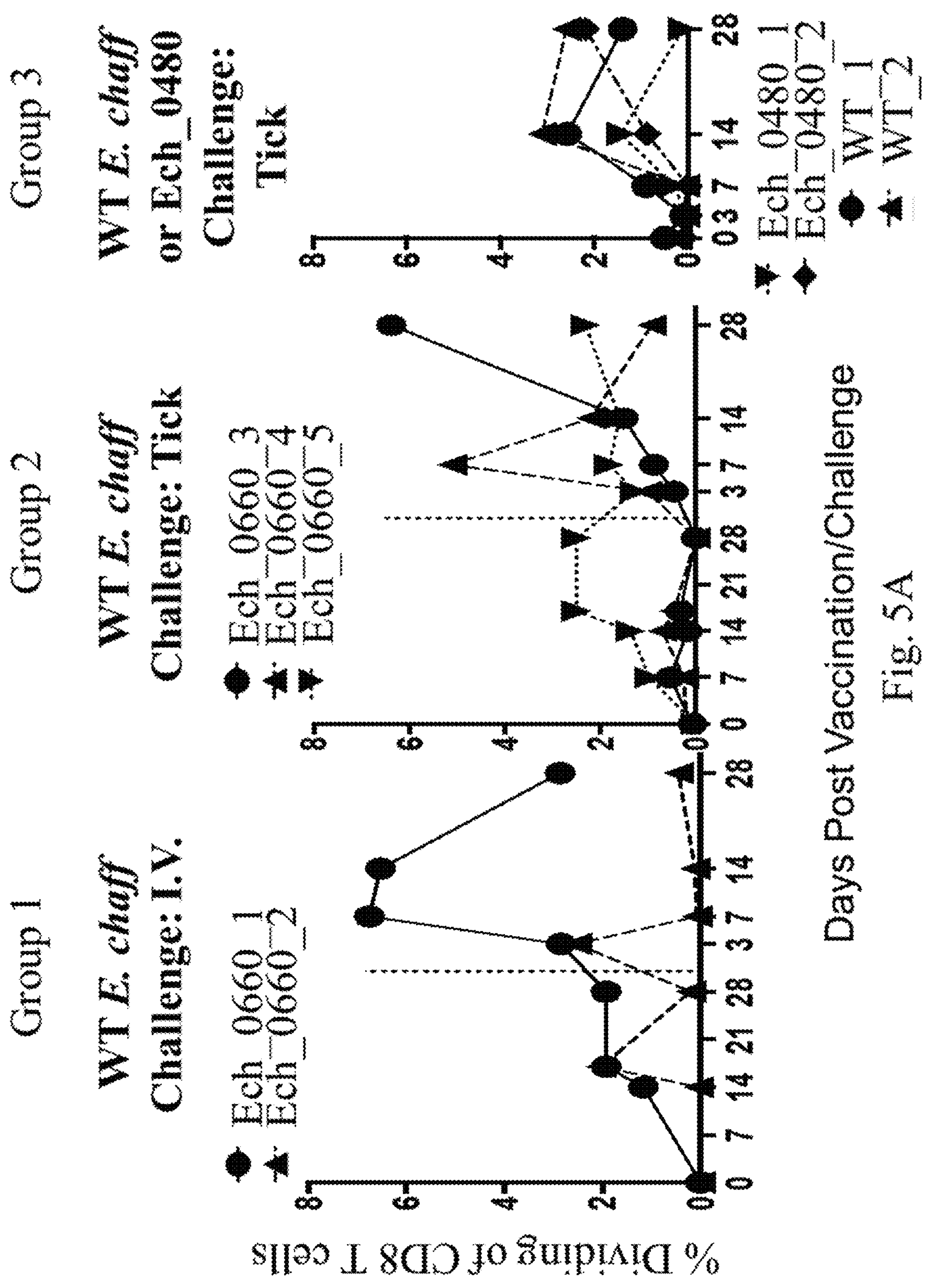
FIG. 5A shows data from $CD8^+$ T cells were analyzed by flow cytometry for proliferation as measured by Cell Trace Violet dilution at day 5 of culture.
Figure 5B:
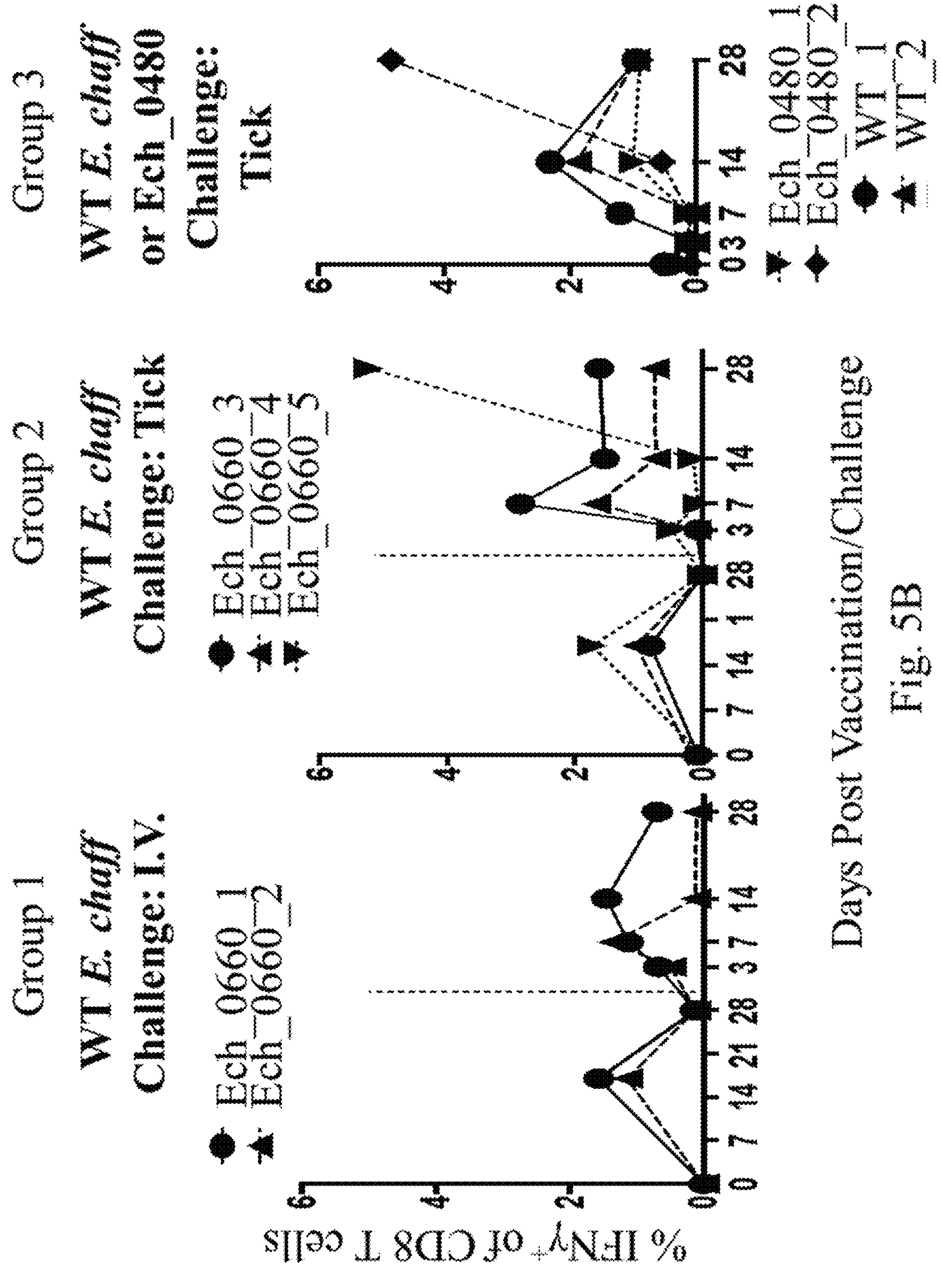
FIG. 5B shows data from intracellular production of IFNγ at day 5.

FIG. 5 presents $CD8^+$ T cell proliferation and IFNγ production were measured using similar approaches as in FIGS. 3 and 4. PBMC from dogs in groups 1-3 were cultured for 5 days at $4\times10^6$ cells/mL in the presence or absence of 10 ug/mL *E. chaffeensis* host-cell free lysate. On day 5 of culture, $CD8^+$ T cells were analyzed by flow cytometry for proliferation as measured by Cell Trace Violet dilution, illustrated in FIG. 5A; and intracellular production of IFNγ, illustrated in FIG. 5B. The frequencies of responding $CD8^+$ T cells were measured over the course of the experiment. Results were gated on total live cells and total $CD3^+CD8^+$ T cells. Background was subtracted as above.

Neither vaccination nor infection with wild type *E. chaffeensis* induced a significant $CD8^+$ T cell response as measured by proliferation or IFNγ.

ELISAs were performed to measure cytokines using PBMC culture supernatants collected after 5 days of stimulation with 10 μg/mL host-cell free *E. chaffeensis* lysate. IL-4, IFNγ, and IL-17A protein concentrations were determined by commercial ELISA kit (R&D Systems, Minneapolis, Minn.) per manufacturer's instructions to measure Th1, Th2 and Th17 cytokines secreted by PBMC in recall responses to *E. chaffeensis* antigen.

Figure 6:
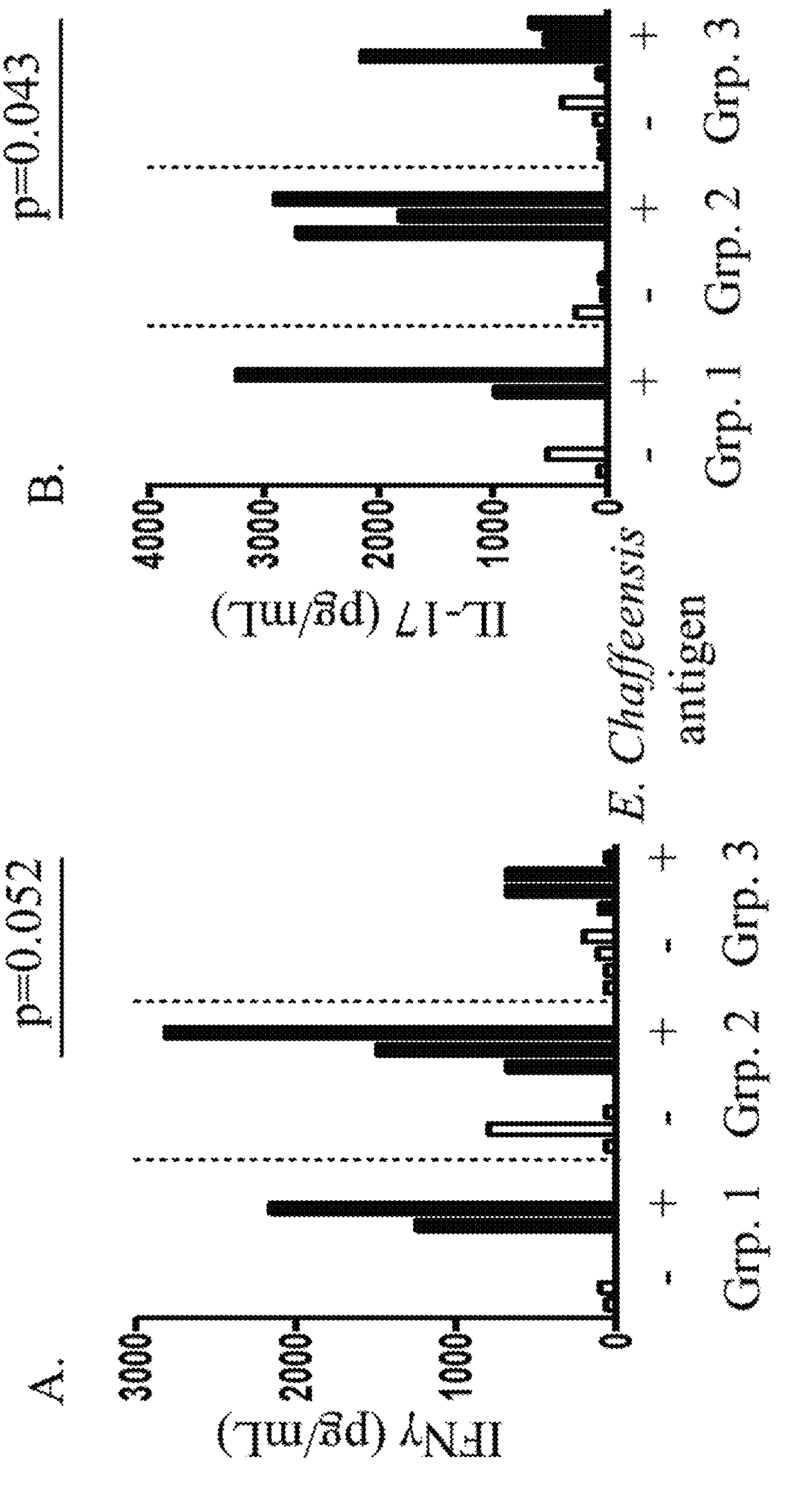
FIG. 6 is data from cell culture supernatants collected and analyzed by Enzyme-linked immunosorbent assay (ELISA) measuring PBMC production of (A) IFNγ and (B) IL-17 following vaccination, challenge, and +/− stimulation with host-cell free *E. chaffeensis* lysate.

FIG. 6 presents PBMC from dogs vaccinated with Ech_0660 and challenged with wild-type *E. chaffeensis* (groups 1-3, as in FIG. 2) were collected on day 7 post-secondary challenge with wild-type *E. chaffeensis*. PBMC were cultured for 5 days at $4\times10^6$ cells/mL in the presence or absence of 10 ug/mL *E. chaffeensis* host-cell free lysate grown in the tick ISE6 cell line. On day 5, cell culture supernatants were collected and later analyzed by ELISA for secretion of (A) IFNγ, (B) IL-17, and IL-4 (not shown). Each bar is representative of a single animal.

PBMC from Ech_0660 vaccinated animals secreted IFNγ (Th1) in response to *E. chaffeensis* antigen (FIG. 6A); and this response was significantly increased over the response from unvaccinated control dogs. We did not observe appreciable IL-4 (Th2) production by PBMC from vaccinated or control dogs (data not shown); however, all three groups mounted a vigorous IL-17 response to *E. chaffeensis* antigen (FIG. 6B). IL-17 production by cells from Ech_0660 vaccinated dogs was significantly increased over unvaccinated controls.

Example 6

Attenuated Mutants Confer Protection Against Wild Type Infection Challenge in Deer and Dogs We reasoned that the attenuation in vertebrate hosts with three gene disruption mutations is the result of the pathogen's inability to maintain replication cycle continuously. We then hypothesized that the attenuated mutants induce sufficient host response to protect against infection challenge with wild type *E. chaffeensis*. We tested this hypothesis with two clonally purified attenuated mutants with insertions within Ech_0379 and Ech_0660 genes, as these mutations caused the loss of gene activity from putative $Na^+/H^+$ antiporter and phage like structure protein, respectively. Five groups of deer were used (three animals each in groups 1, 3 and 4, and two animals each in groups 2 and 5): group 1 received wild type *E. chaffeensis* infection; group 2 received clonally purified Ech_0284 mutant, as it is similar to wild type in causing persistent infection and can serve as a syngeneic positive control for other mutants; groups 3 and 4 received infections with clonally purified Ech_0379 and Ech_0660 mutants, respectively; and group 5 received no infection to serve as non-infection controls. Infection in all five groups was monitored in blood sampled frequently for 31-41 days and by performing nested PCRs on DNA recovered or by culture recovery method (Table 5). Infection was detected frequently and persisted very similar in groups 1 and 2 animals (59% and 61% of the samples tested positive, respectively), while detected less frequently (19% of the time) in Ech_0379 mutant infected (group 3) animals; detected in one animal on day 4 and 28, on day 35 in the second animal, and on day 7 in the third animal. Infection was undetectable throughout the study in group 4 (Ech_0660 mutant group) and group 5 deer (controls).

TABLE 5

White tailed deer Infection status with three different clonally purified mutants or with wild type *E. chaffeensis*[#]

| | | Days post infection* | | | | | | | | | |
|---|---|---|---|---|---|---|---|---|---|---|---|
| | | 0 | 4 | 11 | 18 | 22 | 24 | 27 | 30 | 37 | 41 |
| Group 1 | wt-1 | − | − | + | + | + | + | + | + | + | + |
| | wt-2 | − | − | − | − | + | + | + | + | + | − |
| | wt-3 | − | + | − | − | − | + | + | − | − | − |
| | | 0 | 3 | 5 | 8 | 10 | 14 | 21 | 23 | 28 | 31 |
| Group 2 | Ech__0284-1 | − | − | + | + | + | + | + | − | − | − |
| | Ech__0284-2 | − | − | − | + | + | + | + | + | − | + |
| | | 0 | 4 | 7 | 12 | 14 | 21 | 28 | 35 | | |
| Group 3 | Ech__0379-1 | − | + | − | − | − | − | + | − | | |
| | Ech__0379-2 | − | − | − | − | − | − | − | + | | |
| | Ech__0379-3 | − | − | + | − | − | − | − | − | | |
| | | 0 | 3 | 5 | 8 | 10 | 14 | 21 | 23 | 28 | 31 |
| Group 4 | Ech__0660-1 | − | − | − | − | − | − | − | − | − | − |
| | Ech__0660-2 | − | − | − | − | − | − | − | − | − | − |
| | Ech__0660-3 | − | − | − | − | − | − | − | − | − | − |
| Group 5 | Control-1 | − | − | − | − | − | − | − | − | − | − |
| | Control-2 | − | − | − | − | − | − | − | − | − | − |

[#]The signs − and + refer to samples tested negative or positive by culture recovery and/or nested PCR, respectively.

*Samples were collected on different days post infection for each group. Total average positives in groups 1-5 are 59%, 61%, 19%, 0% and 0%, respectively (0 day data were not included in this calculation).

Plasma samples from all deer in groups 1-5 were evaluated by ELISA for the total IgG antibody response against *E. chaffeensis* whole cell antigens (FIG. 7).

ELISA was performed using a preparation of host cell-free *E. chaffeensis* lysate. Plasma samples from deer or dogs collected prior to infection and several days following infections were assessed by ELISA for the presence of the pathogen-specific IgG.

Figure 7A:
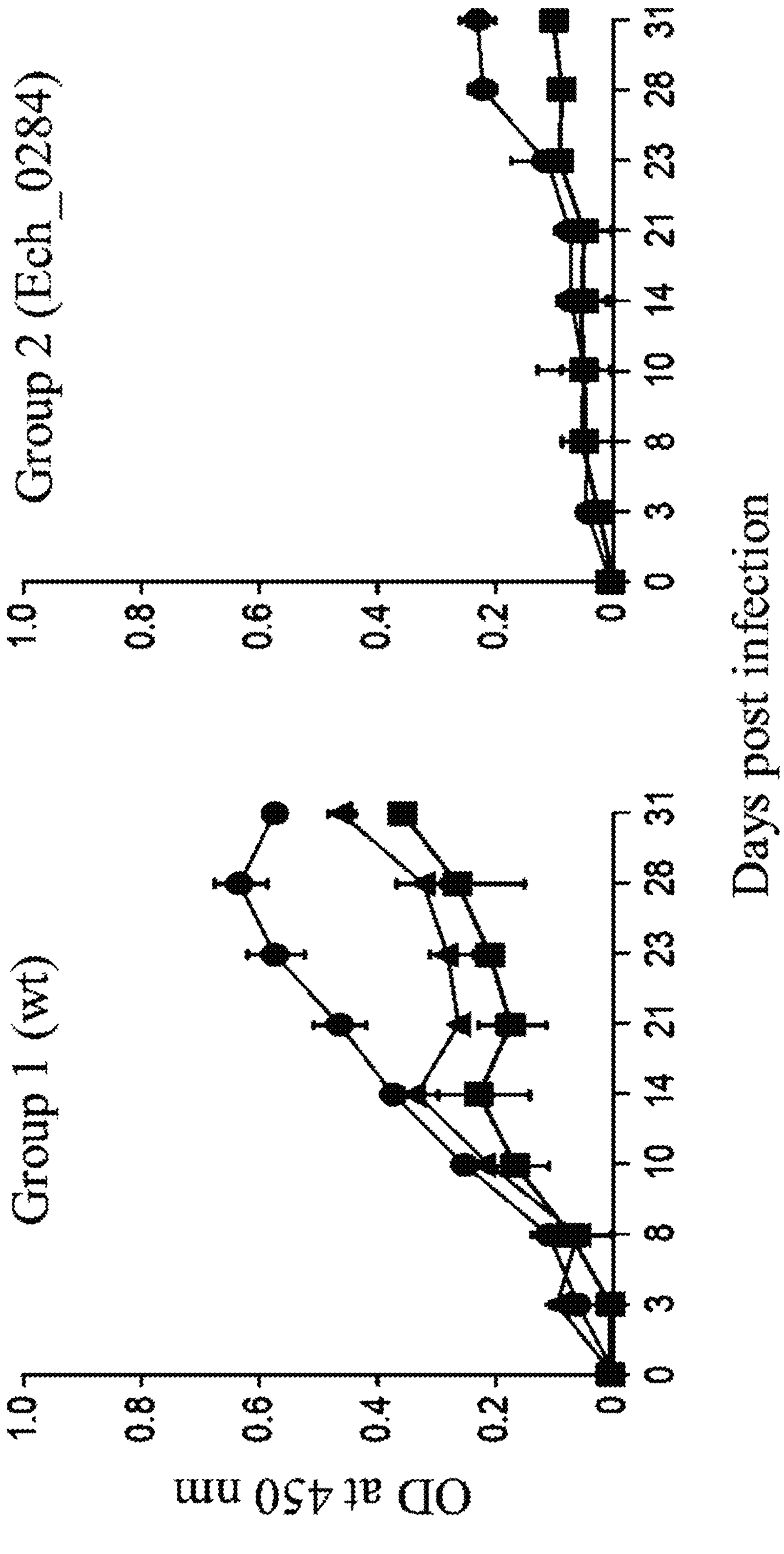
FIG. 7A shows data from an ELISA measuring Pathogen-specific total IgG response in deer infection following vaccination, challenge, and +/− stimulation with host-cell free *E. chaffeensis* lysate for wild type *E. chaffeensis* or mutant Ech_0284.
Figure 7B:
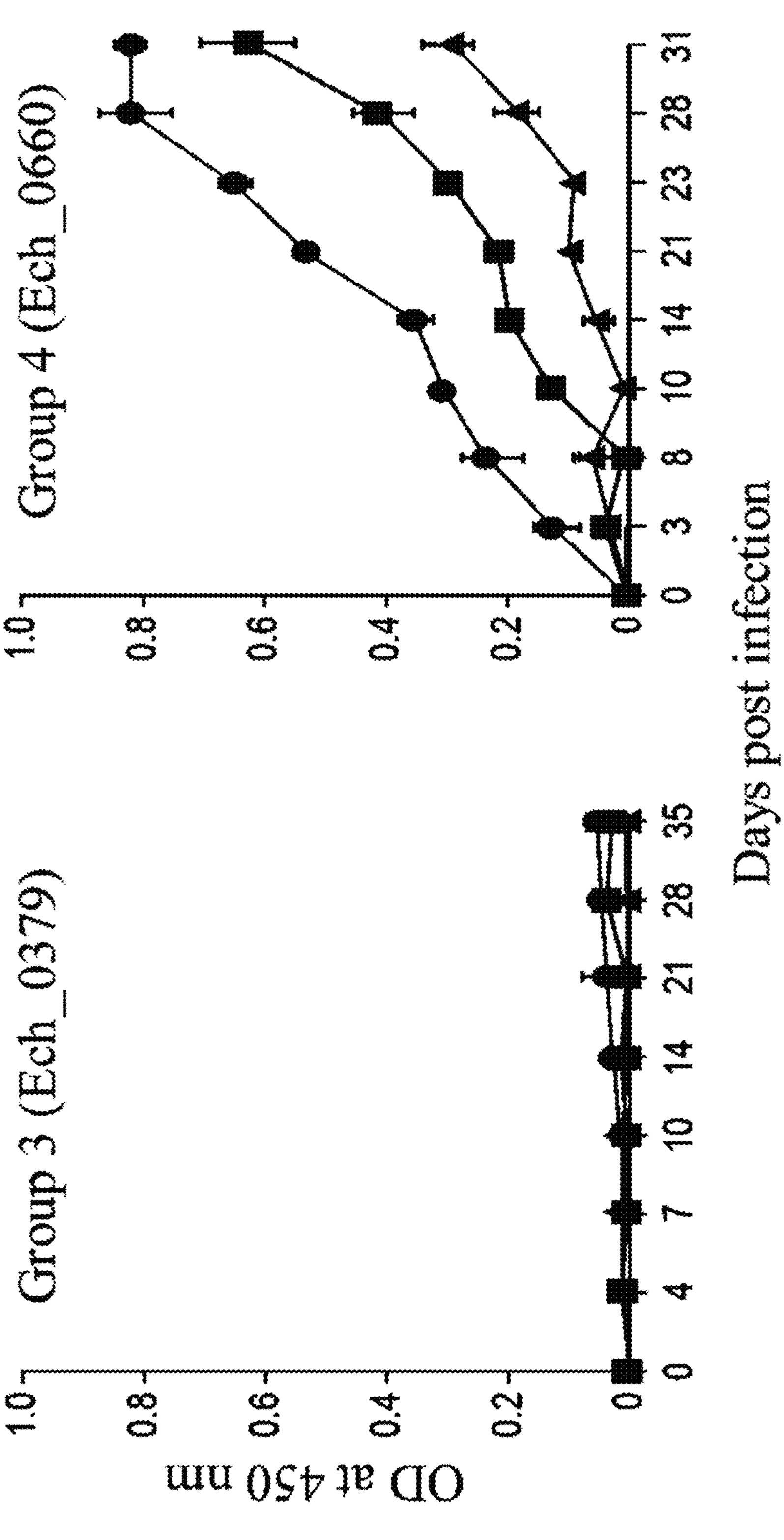
FIG. 7B shows data from an ELISA measuring Pathogen-specific total IgG response in deer infection following vaccination, challenge, and +/− stimulation with host-cell free *E. chaffeensis* lysate for mutant Ech_0379 or Ech_0660.
Figure 7C:
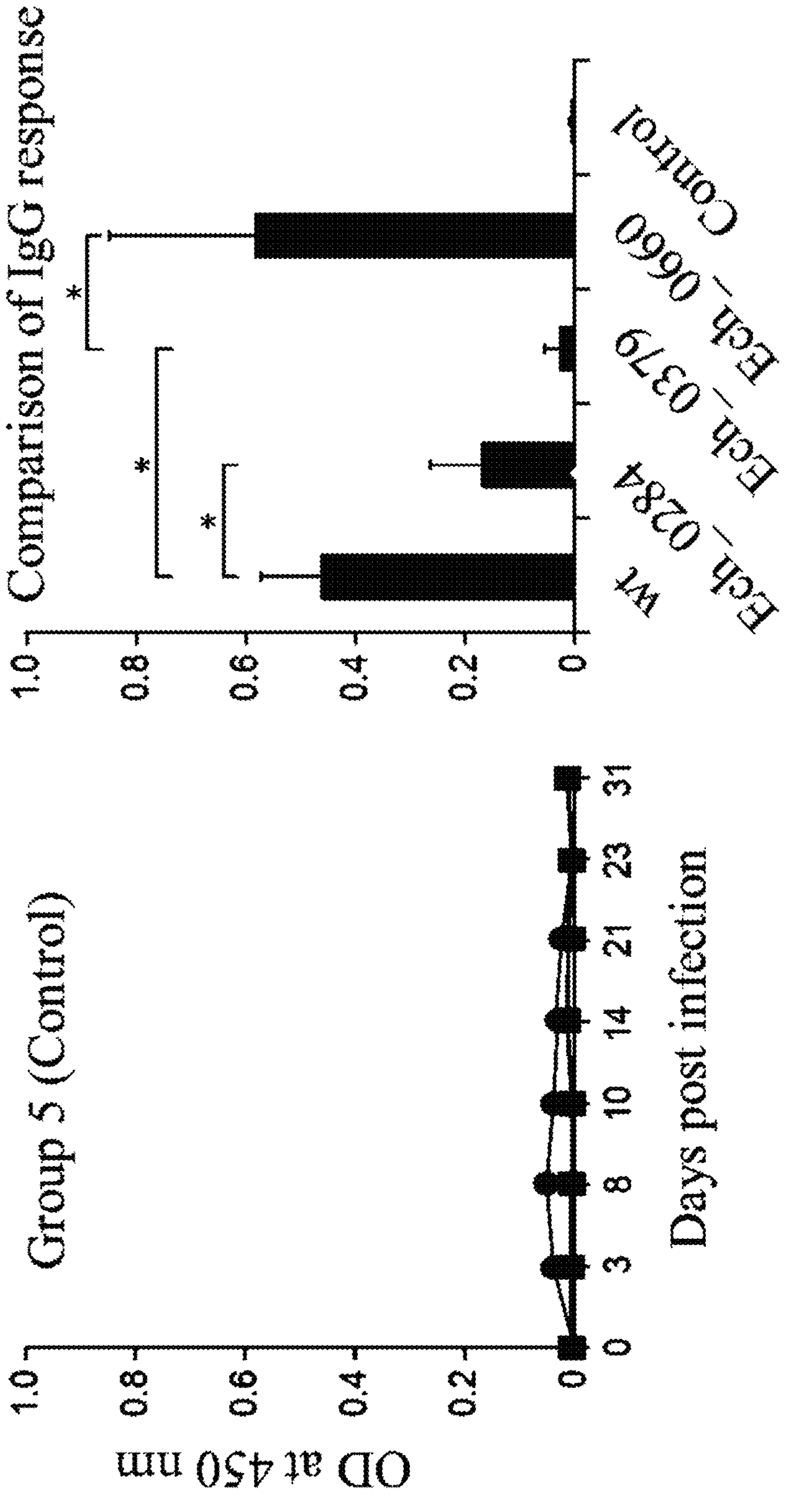
FIG. 7C shows data from an ELISA measuring Pathogen-specific total IgG response in deer infection following vaccination, challenge, and +/− stimulation with host-cell free *E. chaffeensis* lysate for the control, and a graph including comparison of the IgG responses.

FIGS. 7A-7C present *E. chaffeensis*-specific IgG response in deer infected with wild-type and mutant *E. chaffeensis*. Groups 1-5 represent the ELISA analysis performed on animals infected with wild-type, Ech_0284, Ech_0379, Ech_0660 and non-infected controls, respectively. Line graphs within each group represent the IgG responses for individual animals {data presented as mean values±standard deviation (SD) from triplicate samples}. In FIG. 7C, the comparison of IgG data for each group for the last day of sample analysis is shown on the right. Significant IgG differences (P≤0.05) observed between groups are identified with asterisks. Error bars for this graph represent mean values±SD for animals within each group.

Deer in groups 1 and 4 (wild type and Ech_0660 mutant infected groups, respectively) had IgG responses, whereas the Ech_0379 infected group 3 and control group 5 had no IgG responses. The Ech_0284 infected group 2 had a weaker response. The IgG levels are higher in wild type infected group which steadily increased with time post infection. The IgG responses were similar for wild type and Ech_0660 infected animals. The IgG levels for these two groups were not significantly different, as judged by comparing the IgG data for each group for the last day of the sample analysis, while IgG in Ech_0284 and Ech_0379 mutant infected animals were significantly lower compared to wild type. Similarly, Ech_0379 and Ech_0660 mutant infected animals differed significantly ($P \leq 0.05$).

To determine if the Ech_0379 and Ech_0660 mutants confer protection, deer infected with these mutants (groups 3 and 4, respectively) were intravenous infection challenged with wild type *E. chaffeensis* after about a month and the infection was monitored in blood by nested PCR and by in vitro culture recovery methods for 32 days (group 3) or 44 days (group 4) (Table 6). To serve as a positive control, infection in deer with the wild type *E. chaffeensis* infection (group 1 above) was carried out with this challenge experiment using the inoculum used from same batch of culture. All three challenged animals in the Ech_0660 group tested negative for the organism for the entire 44 days, while one animal in the Ech_0379 group tested positive on day 7 post challenge (Table 6). In toto, prior exposure of animals with the attenuated mutants; Ech_0379 or Ech_0660, reduced *E. chaffeensis* circulating in blood when challenged with wild type organisms. Tissue samples (liver and spleen) collected at the end point of the study were assessed for the presence of *E. chaffeensis* by nested PCR. DNA was isolated from about 20 mg each of a tissue sample and nested PCR assays were performed as described above in Example 1 above.

TABLE 6

Assessing Ech_0379 and Ech_0660 mutant in conferring protection against *E. chaffeensis* challenge in white-tailed deer#

| | | Days post challenge | | | | | |
|---|---|---|---|---|---|---|---|
| | | 4 | 7 | 12 | 19 | 23 | 32 |
| Group 3 | Ech_0379-1 | − | + | − | − | − | − |
| | Ech_0379-2 | − | − | − | − | − | − |
| | Ech_0379-3 | − | − | − | − | − | − |

| | | 4 | 11 | 18 | 22 | 24 | 27 | 30 | 34 | 37 | 41 | 44 |
|---|---|---|---|---|---|---|---|---|---|---|---|---|
| Group 4 | Ech_0660-1 | − | − | − | − | − | − | − | − | − | − | − |
| | Ech_0660-2 | − | − | − | − | − | − | − | − | − | − | − |
| | Ech_0660-3 | − | − | − | − | − | − | − | − | − | − | − |

#The signs − and + refer to samples tested negative or positive by culture recovery and/or nested PCR, respectively.

Figure 8A:
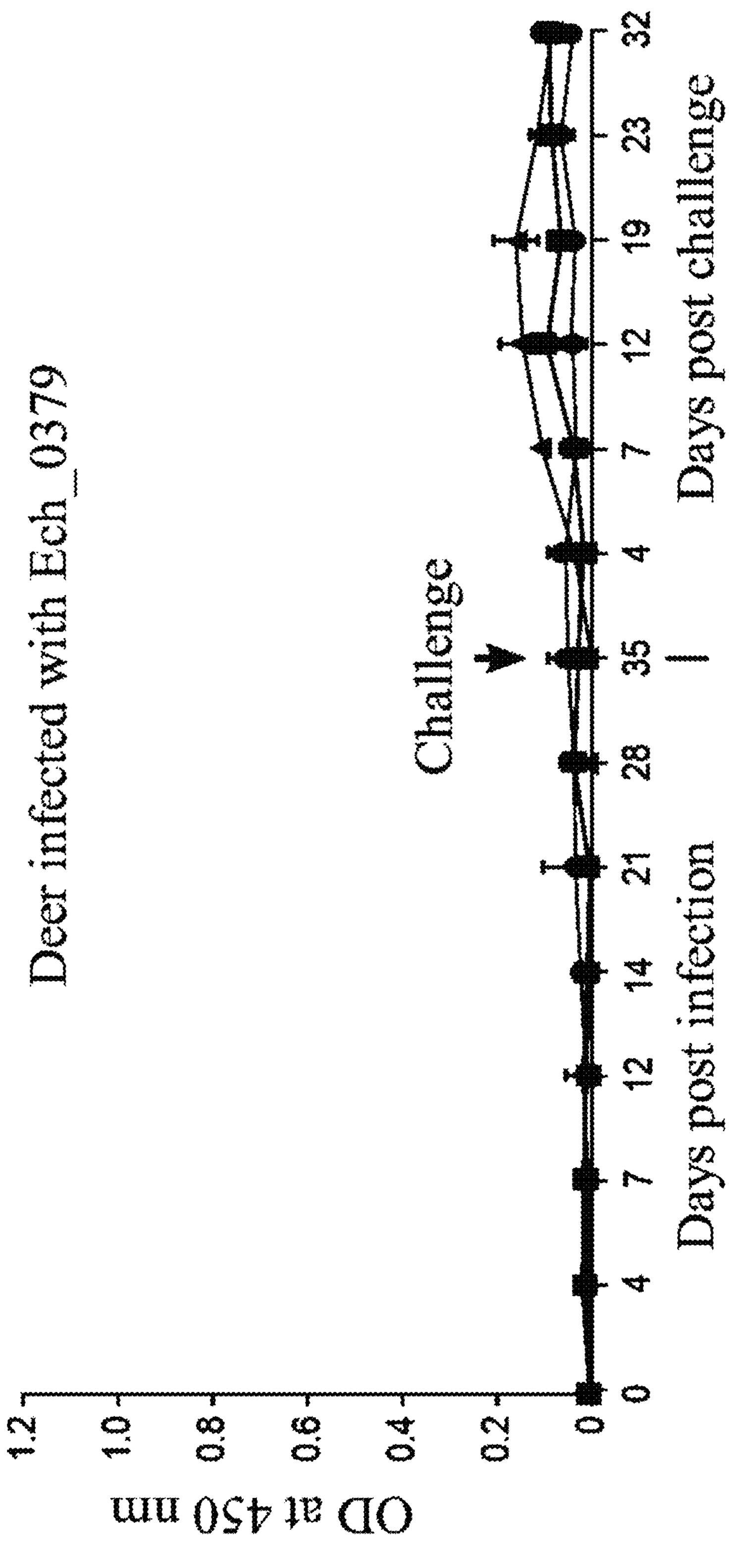
FIG. 8A is data from an ELISA measuring Pathogen-specific total IgG response in deer following vaccination and subsequent challenge for Ech_0379.
Figure 8B:
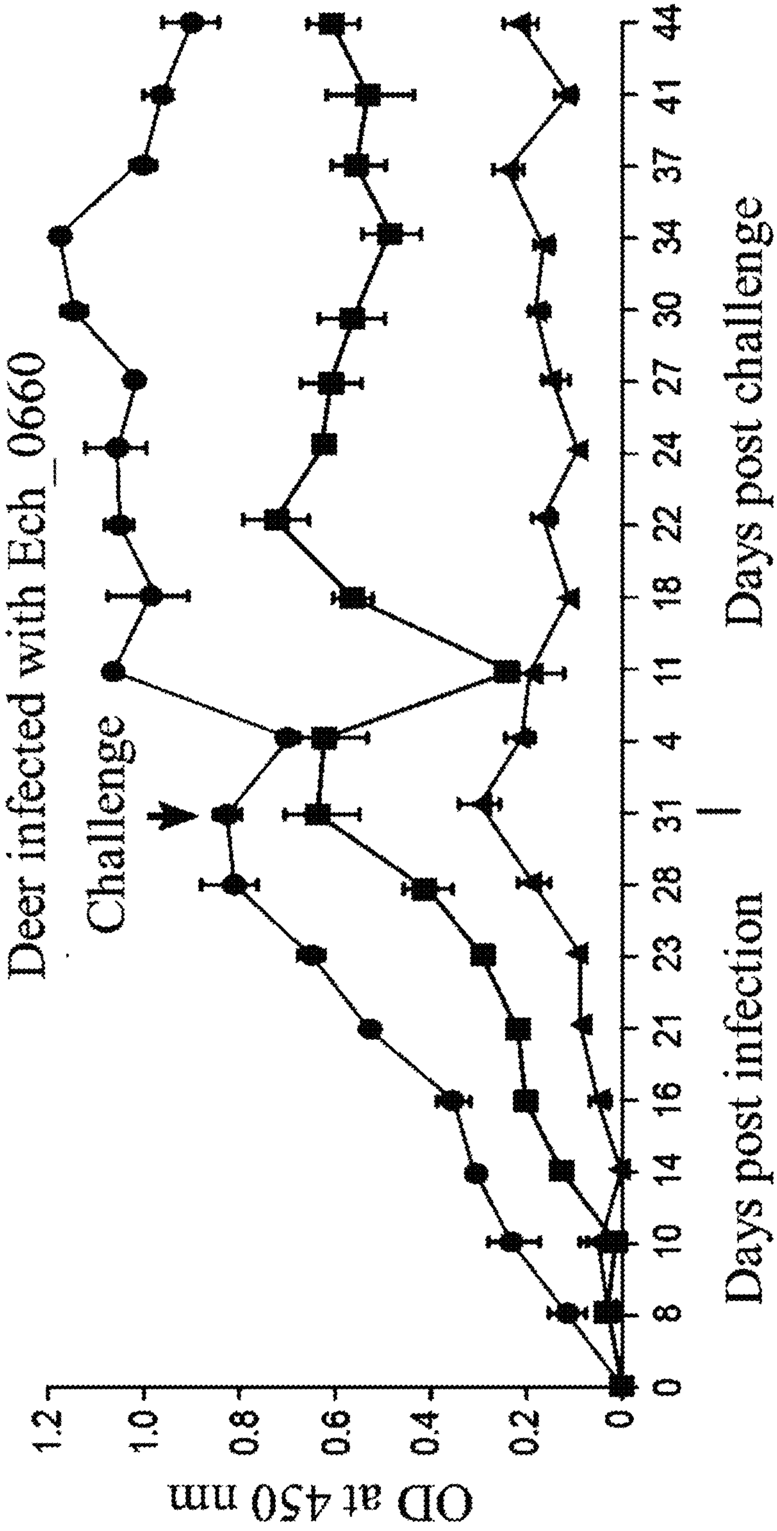
FIG. 8B is data from an ELISA measuring Pathogen-specific total IgG response in deer following vaccination and subsequent challenge for Ech_0660.

Animals in group 4 (Ech_0660 group) and non-infected controls (group 5) tested negative, while deer in groups 1 and 3 (wild type and Ech_0379 groups) tested positive in one or both tissues (Table 7, annotated as above). The group 3 (Ech_0379 group) animals receiving *E. chaffeensis* challenge had a very little change in the antibody response, while two of the three challenged animals in group 4 (Ech_0660 group) had a steady rise in the antibody response (FIG. 8). Specifically, FIGS. 8A-8B present *E. chaffeensis*-specific IgG changes in deer receiving Ech_0379 (FIG. 8A) or Ech_0660 (FIG. 8B) mutant followed by challenge with wild-type infection. IgG levels were assessed in animals receiving mutant inoculated and challenged with wild-type for several days post infection. The data were plotted as in FIG. 3. The day of challenge is identified with down arrows.

TABLE 7

Infection status of tissue samples in deer (Note: the deer numbers are the same as in Table 5)#

| | Deer Group | | | | | | | | | | |
|---|---|---|---|---|---|---|---|---|---|---|---|
| | 1 (wild type) | | | 3 (Ech_0379) | | | 4 (Ech_0660) | | | 5 (Control) | |
| Tissue | 1 | 2 | 3 | 1 | 2 | 3 | 1 | 2 | 3 | 1 | 2 |
| Spleen | + | + | − | + | + | − | − | − | − | − | − |
| Liver | + | + | + | + | − | − | − | − | − | − | − |

#The − and + signs refer to samples tested negative or positive by nested PCR, respectively.

The infection and challenge experiment was repeated in dogs using mutant/vaccine candidates Ech_0379 and Ech_0660. Tick transmission protocol was performed as follows. *E. chaffeensis* infected *A. americanum* adult ticks were used for the tick-transmitted challenge. The tick infection was conducted as previously described. Briefly, nymphal ticks were needle-inoculated with 5 μl of concentrated bacterial culture containing of ~5,000 wild-type *E. chaffeensis* or virulent Ech_0480 mutant. Nymphs were allowed to molt into adults at room temperature in a humidified chamber with 14 h daylight and 10 h darkness cycles. The infection status of the needle-inoculated ticks was verified by nested PCR targeting to the Ech_1136 gene encoding for the p28-Omp 14 protein as previously described. A small area on the back of the dog was shorn and a tick containment cell was affixed. Twenty-five pairs of adult ticks per dog were placed in the tick containment cell and permitted to feed for 6-7 days before removal.

Two dogs each were infected with the two mutants or with wild type *E. chaffeensis* and two dogs were kept as uninfected controls. Infection with wild type and uninfected controls were as previously described. Infection in blood was monitored by nested PCR and culture recovery methods. The wild type *E. chaffeensis* infected dogs were persistently positive (83% of the time), while the uninfected controls tested negative for the same time period. One dog receiving infection with the Ech_0379 mutant tested positive on days 3, 7 and 10 and the second dog tested positive on days 3, 10, 15, 30, 32 and 35 (Table 8).

TABLE 8

Assessing Ech_0379 and Ech_0660 mutants in conferring protection against wild type *E. chaffeensis* challenge in dogs[#]

| | Days Post Infection | | | | | | | | | | | Days Post Challenge | | | | | | |
|---|---|---|---|---|---|---|---|---|---|---|---|---|---|---|---|---|---|---|
| | 0 | 3 | 7 | 10 | 15 | 18 | 22 | 24 | 30 | 32 | 35* | 2 | 8 | 10 | 17 | 24 | 31 | 38 |
| Ech_0379-1 | – | + | + | + | – | – | – | – | – | – | – | + | + | + | – | – | – | – |
| Ech_0379-2 | – | + | – | + | + | – | – | – | + | + | + | – | + | + | + | – | – | – |

| | 0 | 5 | 7 | 9 | 12 | 14 | 16 | 19 | 21 | 26 | 29* | 5 | 8 | 10 | 14 | 20 | 22 | 28 | 35 | 42 | 49 | 56 | 64 |
|---|---|---|---|---|---|---|---|---|---|---|---|---|---|---|---|---|---|---|---|---|---|---|---|
| Ech_0660-1 | – | + | + | – | – | – | – | – | – | – | + | + | – | – | – | – | – | – | – | – | – | – | – |
| Ech_0660-2 | – | – | + | – | – | – | – | – | – | – | – | – | – | – | – | – | – | – | + | – | – | – | – |

[#]The signs – and + refer to samples tested negative or positive by culture recovery and/or nested PCR, respectively.

Both the dogs receiving Ech_0660 mutant infection tested positive only for the first week after receiving the inoculum (positives detected on days 2 and 7 for one dog and day 7 for the second dog) (Table 8). One dog infected with Ech_0660 mutant also tested positive by culture recovery on day 29 post infection. Dogs infected with Ech_0379 and Ech_0660 mutants were challenged after about a month with wild type *E. chaffeensis.*

Figure 9A:
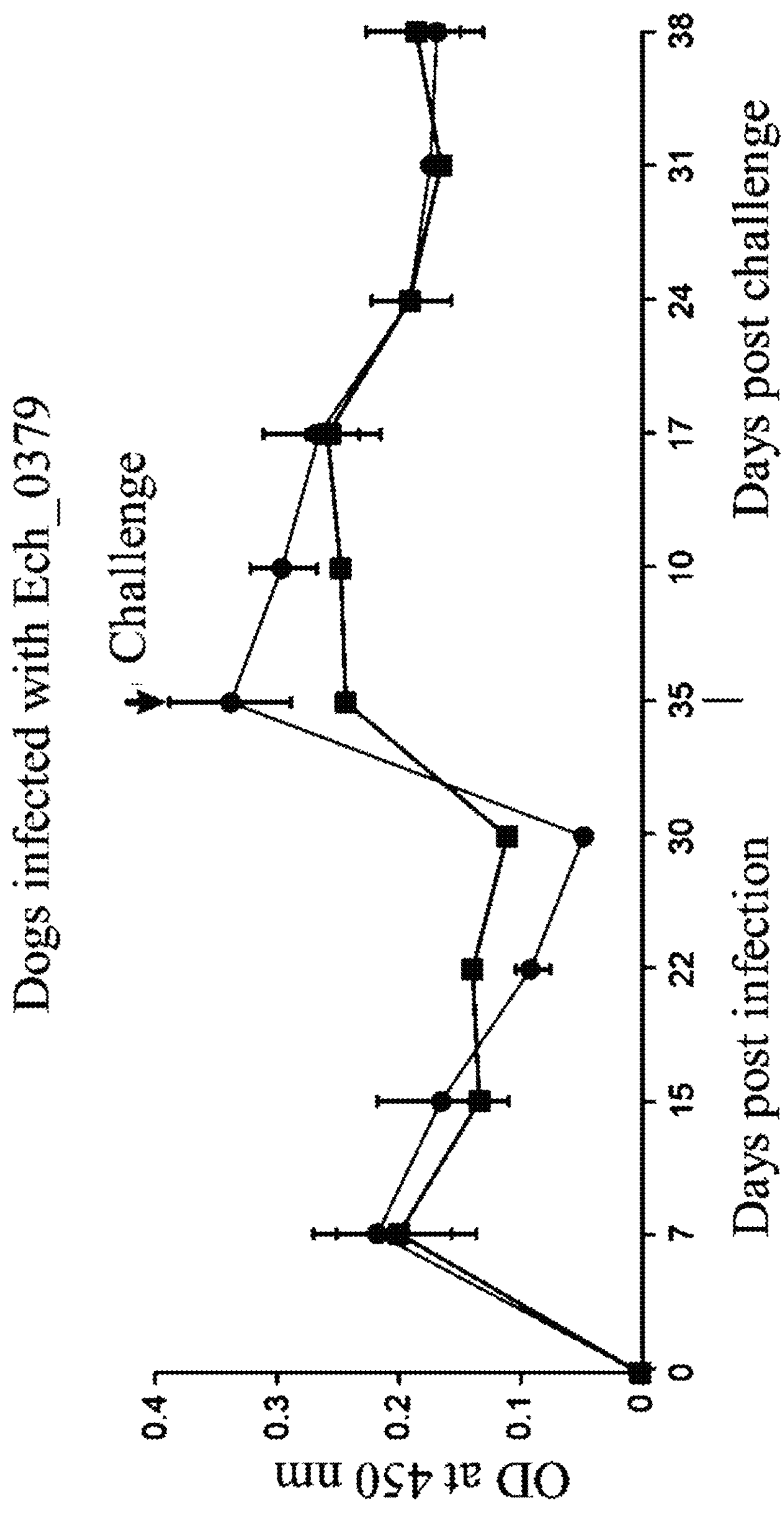
FIG. 9A is data from an ELISA measuring Pathogen-specific total IgG response in dogs following vaccination and subsequent challenge for Ech_0379.
Figure 9B:
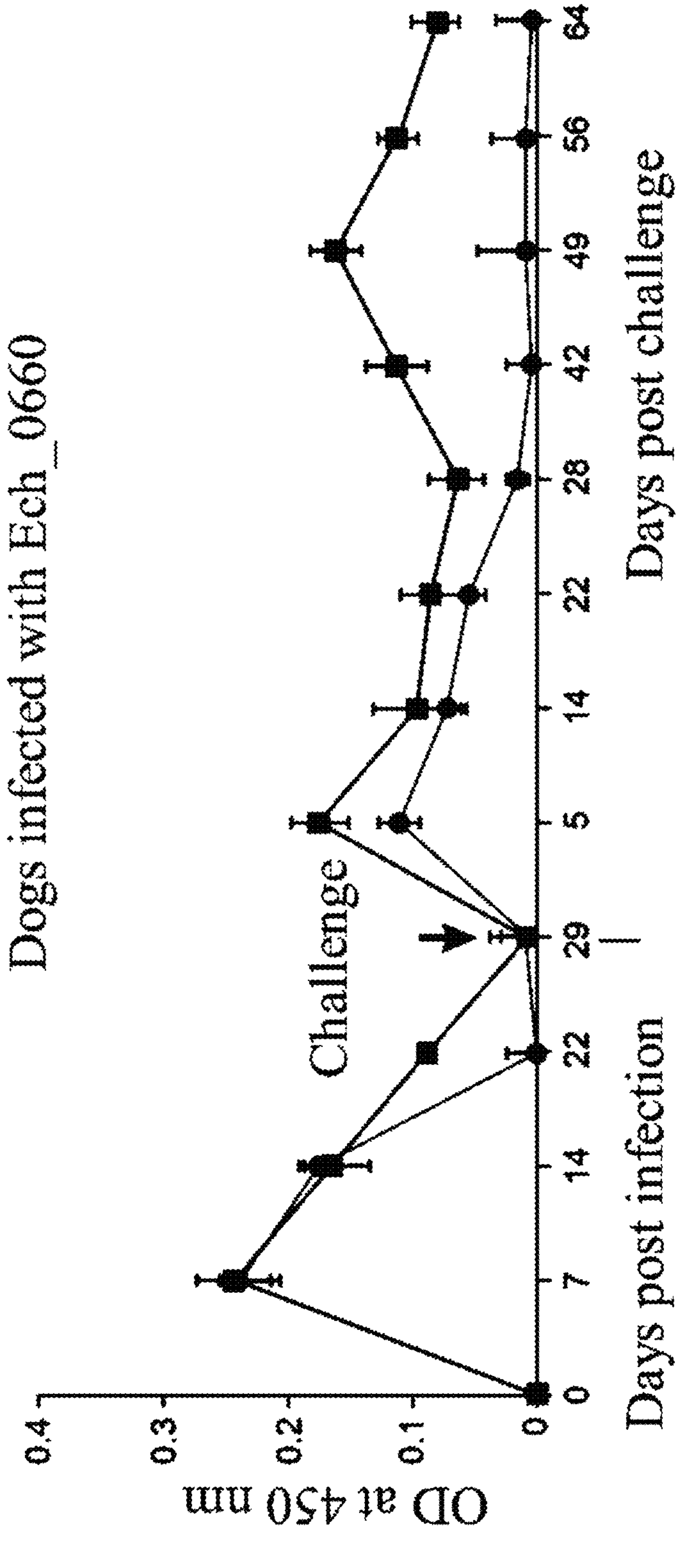
FIG. 9B is data from an ELISA measuring Pathogen-specific total IgG response in dogs following vaccination and subsequent challenge for Ech_0660.

The infection was monitored in blood sampled up to 38 days (Ech_0379 mutant group) or 64 days (Ech_0660 mutant group) (Table 8). The Ech_0660 mutant group tested negative all days after infection challenge, except for the first week in one dog, while the Ech_0379 mutant group challenged dogs tested positive more frequently for the first 17 days post-challenge. DNA recovered from spleen and liver samples from the challenged group dogs at the end point of the study for both the groups tested negative for the organism, while dogs received only wild type infection tested positive (not shown). FIGS. 9A-9B illustrate *E. chaffeensis*-specific IgG response in dogs with Ech_0379 (FIG. 9A) or Ech_0660 (FIG. 9B) mutant followed by challenge with wild-type *E. chaffeensis*. IgG levels assessed in animals receiving mutant inoculated and challenged with wild-type for several days post infection. The data were plotted as in FIG. 3. The day of challenge is identified with down arrows; dogs in both groups had a rise and fall in pathogen-specific IgG responses following mutant infections; and the responses were boosted initially with wild type infection challenges and then declined with time.

To determine if the Ech_0660 mutant is protective in a physiologic setting of tick-transmitted challenge, we vaccinated dogs with the mutant and then performed secondary challenges on day 31-post infection. Four control dogs remained unvaccinated. Seven dogs were vaccinated i.v. with the Ech_0660 mutant organisms. Animals were monitored for the presence of *Ehrlichia* in the blood following Ech_0660 vaccination by PCR and culture recovery methods (Table 9).

TABLE 9

Infection status of dogs vaccinated with attenuated mutant Ech_0660

| | Days Post Vaccination | | | | | | | |
|---|---|---|---|---|---|---|---|---|
| | 0 | 3 | 8 | 11 | 14 | 21 | 28 | 31 |
| Ech_0660_1[a] | – | – | – | – | – | – | – | – |
| Ech_0660_2 | – | – | – | – | – | – | – | – |
| Ech_0660_3 | – | c[b] | – | – | – | – | – | – |
| Ech_0660_4 | – | – | – | – | – | – | – | – |

TABLE 9-continued

Infection status of dogs vaccinated with attenuated mutant Ech_0660

| | Days Post Vaccination | | | | | | | |
|---|---|---|---|---|---|---|---|---|
| | 0 | 3 | 8 | 11 | 14 | 21 | 28 | 31 |
| Ech_0660_5 | – | – | – | – | – | – | – | – |
| Ech_0660_6 | – | c | – | – | – | – | – | – |
| Ech_0660_7 | – | c | – | – | – | – | – | – |

[a]Seven dogs were inoculated i.v. with $2 \times 10^8$ *E. chaffeensis* mutant Ech_0660 organisms.
[b]Dogs were tested at the indicated time points for *E. chaffeensis* organisms in the blood by PCR (p) and culture recovery methods (c) as previously described.

We have shown previously that the Ech_0660 mutant is highly attenuated and rapidly cleared from the canine host. In agreement with our prior studies, the Ech_0660 mutant was detected in only three animals on day 3 post vaccination. Thirty-one days after vaccination, dogs were divided into groups. Two Ech_0660 vaccinated dogs were challenged with wild-type *E. chaffeensis* via needle inoculation (group 1). Three vaccinated dogs were challenged with wild-type *E. chaffeensis* by tick transmission (group 2). The four unvaccinated control dogs were challenged via tick transmission with wild-type *E. chaffeensis* (n=2) or a wild-type like, isogenic mutant strain Ech_0480 (n=2) (group 3). We have previously demonstrated that the Ech_0480 mutant behaves like the wild-type strain of *E. chaffeensis*, displaying similar persistence in the vertebrate host; therefore we have combined the data for these two control groups (group 3).

*E. chaffeensis* infection in dogs varies from subclinical infection to severe systemic disease. Mild clinical signs may manifest as low-grade fever or thrombocytopenia, as others and we have previously reported. In this experiment, we did not observe significant clinical disease in vaccinated or control dogs (data not shown). *E. chaffeensis* infection was monitored in the blood after secondary challenge using nested PCR and culture recovery methods. The results are shown in Table 10. Dogs that were vaccinated and challenged with wild-type *E. chaffeensis* by needle inoculation (group 1) were protected from infection, as evidenced by testing positive for infection in the blood only twice in one animal on days 8 and 11 post challenge (12.5% of the time), and testing negative for the organism in the spleen and liver at the time of necropsy. Vaccinated dogs that were challenged via tick-transmission (group 2) were also protected from secondary challenge. This group tested positive for

*Ehrlichia* in the blood 29.1% of the time (7 out of 24 total blood samples tested). However, no blood positives were obtained after day 15 post challenge, and all animals were also negative for the organism in the spleen and liver at the time of necropsy. This result suggests that while dogs may develop ehrlichemia early following infection, vaccination with the Ech_0660 mutant promotes protection from long-term pathogen persistence in the blood and organs. In contrast, unvaccinated control dogs (group 3) displayed persistent infection, testing frequently positive for the organism throughout the 31 days of assessment (about 34.3% of the time: 11 out of 32 samples tested) and moreover testing positive for the organism in the tissues at necropsy.

TABLE 10

Infection status of Ech_0660 vaccinated dogs and unvaccinated control dog following wild type *E. chaffeensis* challenge

| | Days Post Challenge: WT *E. chaffeensis* by needle transmission | | | | | | | | Necropsy[e] | | |
|---|---|---|---|---|---|---|---|---|---|---|---|
| Group 1[a] | 0 | 4 | 8 | 11 | 15 | 22 | 29 | 36 | blood | sp | liv |
| Ech_0660_1 | – | – | – | – | – | – | – | – | – | – | – |
| Ech_0660_2 | – | – | p[d] | c | – | – | – | – | – | – | – |
| | Days Post Challenge: WT *E. chaffeensis* by tick transmission | | | | | | | | | | |
| Group 2[b] | 0 | 4 | 8 | 11 | 15 | 22 | 29 | 36 | blood | sp | liv |
| Ech_0660_3 | – | – | c | – | c | – | – | – | – | – | – |
| Ech_0660_4 | – | – | c | – | c | – | – | – | – | – | – |
| Ech_0660_5 | – | – | p/c | p | c | – | – | – | – | – | – |
| | Days Post Infection (non-vaccinated control group): WT *E. chaffeensis* or Ech_0480 by tick transmission | | | | | | | | | | |
| Group 3[c] | 0 | 3 | 7 | 10 | 14 | 17 | 24 | 31 | blood | sp | liv |
| Wild-type_1 | – | – | p | – | c | – | – | p | – | – | + |
| Wild-type_2 | – | – | p | – | c | p | – | – | – | – | – |
| Ech_0480_1 | – | – | – | – | c | – | – | – | – | – | + |
| Ech_0480_2 | – | p | – | – | c | – | p | p | – | + | – |

[a]Dogs from Table 9 were challenged 31 days after vaccination. Animals were challenged via i.v. inoculation with 2 × $10^8$ wild type *E. chaffeensis* organisms;

[b]Dogs from Table 9 were challenged 31 days after vaccination. Animals were challenged via tick-transmission with wild type *E. chaffeensis* organisms;

[c]Unvaccinated control dogs were challenged with 2 × $10^8$ wild type *E. chaffeensis* organisms or 2 × $10^8$ Ech_0480 mutant *E. chaffeensis* organisms;

[d]Dogs were tested at the indicated time points for *E. chaffeensis* organisms in the blood by PCR (p) and culture recovery methods (c) as described. Animals testing positive by both methods are indicated by (p/c);

[e]Animals were euthanized and necropsied on day 39 post challenge.

To determine if Ech_0660 mutant inoculation protects dogs against a heterologous challenge, we challenged the remaining two Ech_0660 vaccinated animals with a closely related *Ehrlichia* organism, *E. canis*, by needle inoculation (group 4). One unvaccinated control animal was also infected with wild-type *E. canis* by needle inoculation. Dogs in group 4 tested positive for infection in the blood 81.2% of the time (13 out of 16 samples tested), similar to the unvaccinated control animal (Table 11). Importantly, as only two animals were included in this group, additional experiments will be necessary to confirm this result and to achieve statistical significance.

TABLE 11

Infection status of Ech_0660 vaccinated dogs and unvaccinated control dog following wild-type *E. canis* challenge

| | Days Post Challenge: WT *E. canis* by needle transmission | | | | | | | | Necropsy[d] | | |
|---|---|---|---|---|---|---|---|---|---|---|---|
| Group 4[a] | 0 | 4 | 8 | 11 | 15 | 22 | 29 | 36 | blood | sp | liv |
| Ech_0660_6 | – | – | p/c[c] | p/c | p/c | p/c | p/c | p/c | p/c | – | + |
| Ech_0660_7 | – | – | p/c | – | p/c | p/c | p/c | p/c | p/c | – | – |
| | Days Post Challenge: WT *E. canis* by needle transmission | | | | | | | | | | |
| Control[b] | 0 | 3 | 7 | 10 | 14 | 17 | 24 | 31 | blood | sp | liv |
| E_canis_1 | – | p/c | p/c | p/c | p/c | p/c | p/c | p/c | p/c | + | + |

[a]Dogs from Table 9 were challenged 31 days after vaccination. Animals were challenged i.v. with $2 \times 10^8$ wild-type *E. canis* organisms;
[b]Unvaccinated control dog was challenged with ~$2 \times 10^8$ wild-type *E. canis* organisms;
[c]Dogs were tested at the indicated time points for *E. canis* organisms in the blood by PCR (p) and culture recovery methods (c). Animals testing positive by both methods are indicated by (p/c);
[d]Animals were euthanized and necropsied on day 39 post challenge.

A subsequent analysis of the *E. chaffeensis*—specific IgG response of vaccinated vs unvaccinated animals followed by challenge with wild type organisms was performed. Vaccination revealed a pathogen-specific IgG response in 4 of 5 animals (FIG. 10). Both vaccinated and unvaccinated animals exhibited pathogen-specific IgG responses following challenge.

Figure 10A:
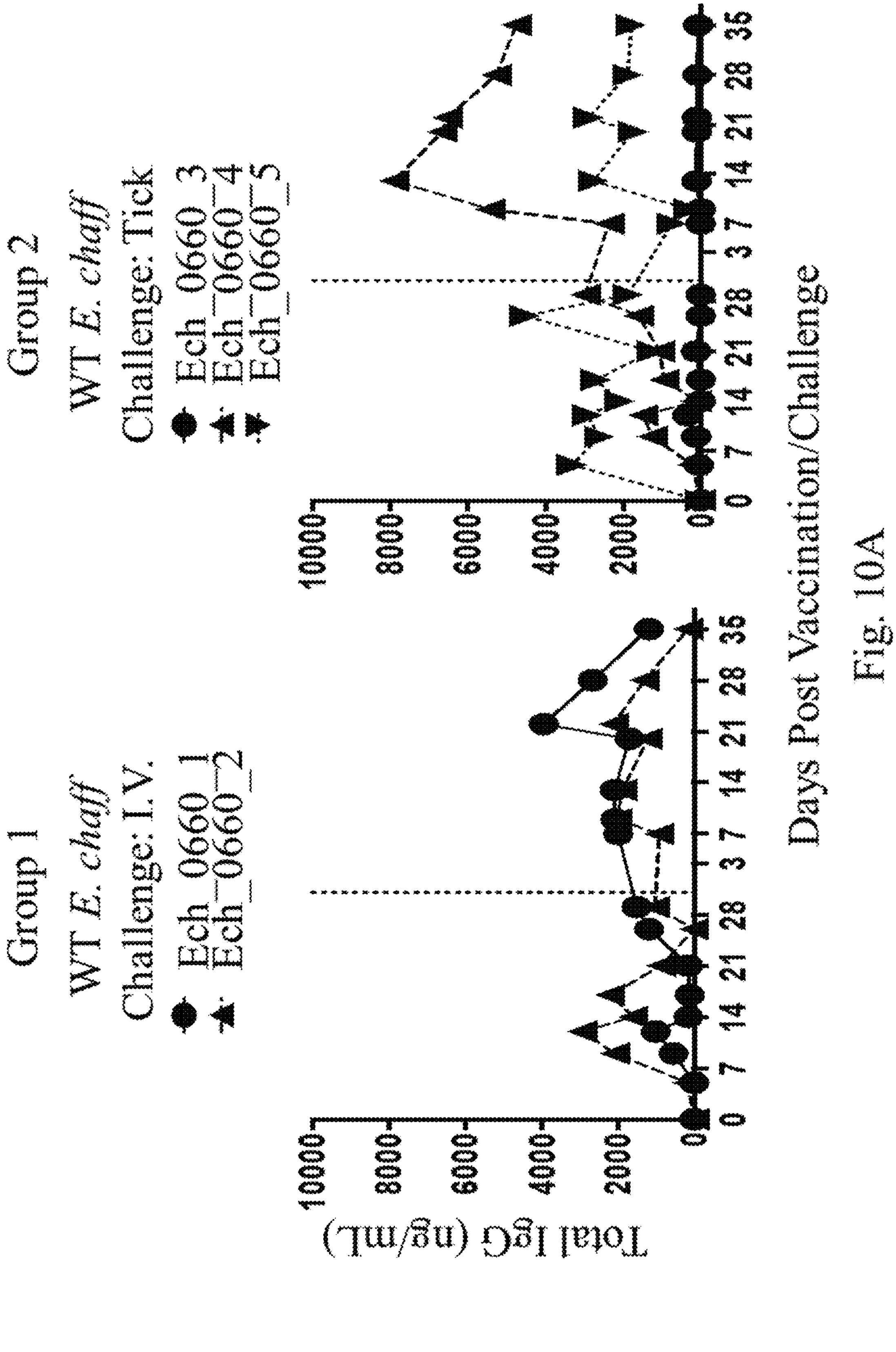
FIG. 10A is data from an ELISA measuring Pathogen-specific total IgG response in deer following vaccination and subsequent challenge delivered by injection vs tick for Ech_0660.
Figure 10B:
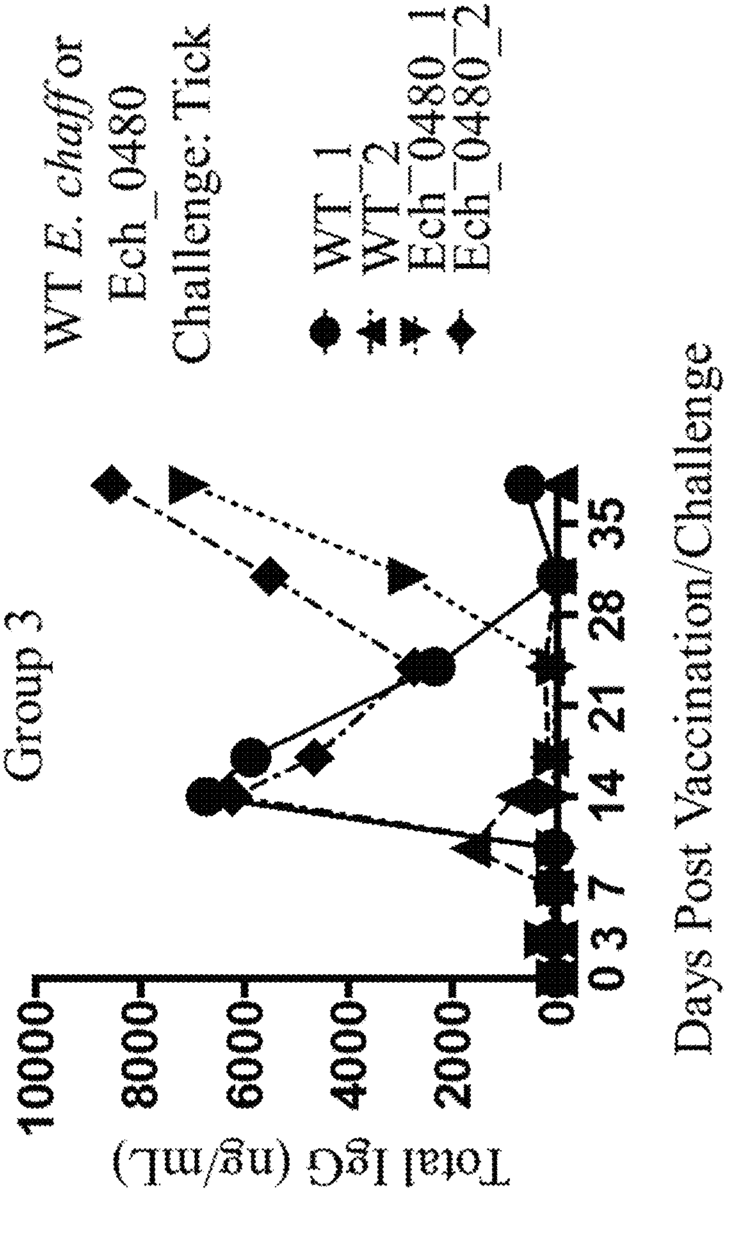
FIG. 10B is data from an ELISA measuring Pathogen-specific total IgG response in deer following vaccination and subsequent challenge delivered by injection vs tick for Ech_0480.

FIG. 10A illustrates total *E. chaffeensis*-specific IgG measured in the plasma at multiple time points by ELISA in dogs vaccinated with the Ech_0660 mutant and challenged with wild type *E. chaffeensis* via needle inoculation (group 1) or vaccinated with Ech_0660 and challenged with wild type *E. chaffeensis* via tick-transmission (group 2). FIG. 10B illustrates unvaccinated control dogs infected with wild type *E. chaffeensis* or the non-attenuated Ech_0480 mutant via tick-transmission (group 3). Each line is representative of a single animal.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10751401B2). An electronic copy of the "Sequence Listing" will also be available from the USPTO upon request and payment of the fee set forth in 37 CFR 1.19(b)(3).

We claim:

1. A method of inducing an immune response against infection by wild type *Ehrlichia chaffeensis* in a mammalian subject, said method comprising administering an effective amount of an immunogenic composition to said subject, said composition comprising live, attenuated *E. chaffeensis* mutant dispersed in a pharmaceutically acceptable carrier, said live, attenuated *E. chaffeensis* mutant comprising a mutation in the Ech_0379 target gene of SEQ ID NO: 4 that results in attenuated growth of the mutant *E. chaffeensis* in the subject, wherein said mutation is an insertion mutation and wherein the immune response reduces the severity of clinical symptoms and/or duration of the *E. chaffeensis* infection upon exposure of the subject to wild type *E. chaffeensis* infection as compared to a corresponding unvaccinated control mammalian subject.

2. The method of claim 1, wherein said administering comprises injecting said immunogenic composition intramuscularly, subcutaneously, intradermally, or intravenously using a needle and syringe, or a needleless injection device.

3. The method of claim 1, wherein said immunogenic composition is administered as a unit dosage form.

4. The method of claim 1, wherein said subject is a non-human mammal.

5. The method of claim 1, wherein said immune response in said subject is selected from the group consisting of *E. chaffeensis*-specific humoral immunity and production of *E. chaffeensis*-specific serum IgG.

6. The method of claim 1, wherein said attenuated *E. chaffeensis* is *E. chaffeensis* strain Arkansas.

7. The method of claim 4, wherein said non-human mammal is a dog or a deer.

8. The method of claim 1, wherein said carrier is selected from the group consisting of normal saline, phosphate buffered saline, sterile water, aqueous dextrose solution, aqueous glycerol solution, ethanol, normal allantoic fluid, oil-in-water or water-in-oil emulsion, dimethyl sulfoxide, and mixtures thereof.

9. The method of claim 1, wherein said infection is tick-transmitted *E. chaffeensis* infection.

10. The method of claim 1, wherein the mutation is an insertion in a protein coding region of the Ech_0379 target gene.

11. The method of claim 1, wherein said insertion comprises insertion of at least one heterologous sequence and optionally insertion of at least one reporter gene stably incorporated therein.

12. The method of claim 1, wherein the mutation comprises insertion of SEQ ID NO: 8 or SEQ ID NO: 9 into the Ech_0379 target gene.

13. The method of claim 1, wherein the mutation in the Ech_0379 target gene results in the mutated gene of SEQ ID NO: 11.

14. The method of claim 1, wherein said mutation results in inhibition and/or inactivation of transcription and/or translation of the gene product of SEQ ID NO: 5.

* * * * *